(12) United States Patent
Geusen

(10) Patent No.: US 10,583,020 B2
(45) Date of Patent: Mar. 10, 2020

(54) BALLOON ASSISTED ENDOLUMINAL PROSTHESIS DEPLOYMENT

(71) Applicant: TRIVASCULAR, INC., Santa Rosa, CA (US)

(72) Inventor: Mark Geusen, Santa Rosa, CA (US)

(73) Assignee: TRIVASCULAR, INC., Santa Rosa, CA (US)

(*) Notice: Subject to any disclaimer, the term of this patent is extended or adjusted under 35 U.S.C. 154(b) by 207 days.

(21) Appl. No.: 15/576,241

(22) PCT Filed: May 26, 2016

(86) PCT No.: PCT/US2016/034427
§ 371 (c)(1),
(2) Date: Nov. 21, 2017

(87) PCT Pub. No.: WO2016/191602
PCT Pub. Date: Dec. 1, 2016

(65) Prior Publication Data
US 2018/0140445 A1    May 24, 2018

Related U.S. Application Data

(60) Provisional application No. 62/167,247, filed on May 27, 2015.

(51) Int. Cl.
*A61F 2/958*    (2013.01)
*A61F 2/07*    (2013.01)
(Continued)

(52) U.S. Cl.
CPC .............. *A61F 2/958* (2013.01); *A61F 2/07* (2013.01); *A61F 2/966* (2013.01);
(Continued)

(58) Field of Classification Search
CPC .. A61F 2/07; A61F 2/958; A61F 2/966; A61F 2002/065; A61F 2002/067;
(Continued)

(56) References Cited

U.S. PATENT DOCUMENTS 4,577,631 A    3/1986 Kremer
5,047,045 A    9/1991 Arney et al.
(Continued)

FOREIGN PATENT DOCUMENTS

CN    1633264 A    6/2005
EP    0621016    10/1994
(Continued)

OTHER PUBLICATIONS

Chinese Office Action dated Jan. 3, 2019, from application No. 201680036853.8.
(Continued)

*Primary Examiner* — George J Ulsh
(74) *Attorney, Agent, or Firm* — Foley & Lardner LLP

(57) ABSTRACT

Delivery system embodiments for treatment of a vascular defect of a patient's vasculature that may include an endoluminal prosthesis loaded on a delivery catheter. In some cases, an inflatable balloon used to facilitate deployment of the endoluminal prosthesis may be disposed within an inner lumen of a tubular graft portion of the endoluminal prosthesis.

16 Claims, 20 Drawing Sheets

(51) Int. Cl.
*A61F 2/966* (2013.01)
*A61F 2/06* (2013.01)
*A61M 25/00* (2006.01)
*A61M 25/10* (2013.01)

(52) U.S. Cl.
CPC ... *A61F 2002/065* (2013.01); *A61F 2002/067* (2013.01); *A61F 2210/0014* (2013.01); *A61F 2220/0016* (2013.01); *A61F 2230/0069* (2013.01); *A61F 2250/0003* (2013.01); *A61F 2250/0098* (2013.01); *A61M 25/0032* (2013.01); *A61M 2025/1004* (2013.01); *A61M 2025/1061* (2013.01)

(58) Field of Classification Search
CPC ...... A61F 2210/0014; A61F 2220/0016; A61F 2230/0069; A61F 2250/0003; A61F 2250/0098; A61M 25/0032; A61M 2025/1004; A61M 2025/1061
See application file for complete search history.

(56) References Cited

U.S. PATENT DOCUMENTS

| | | | |
|---|---|---|---|
| 5,158,548 | A | 10/1992 | Lau et al. |
| 5,219,355 | A | 6/1993 | Parodi et al. |
| 5,534,007 | A | 7/1996 | St. Germain et al. |
| 5,571,087 | A | 11/1996 | Ressemann et al. |
| 5,605,543 | A | 2/1997 | Swanson |
| 5,609,627 | A | 3/1997 | Goicoechea et al. |
| 5,662,703 | A | 9/1997 | Yurek et al. |
| 5,683,452 | A | 11/1997 | Barone et al. |
| 5,749,920 | A | 5/1998 | Quiachon et al. |
| 5,766,203 | A | 6/1998 | Imran et al. |
| 5,968,068 | A | 10/1999 | Dehdashtian et al. |
| 5,976,155 | A | 11/1999 | Foremann et al. |
| 5,980,530 | A | 11/1999 | Willard et al. |
| 6,126,685 | A | 10/2000 | Lenker et al. |
| 6,143,014 | A | 11/2000 | Dehdashtian et al. |
| 6,143,016 | A | 11/2000 | Bleam et al. |
| 6,152,944 | A | 11/2000 | Holman et al. |
| 6,203,550 | B1 | 3/2001 | Olson |
| 6,210,434 | B1 | 4/2001 | Quiachon et al. |
| 6,235,050 | B1 | 5/2001 | Quiachon et al. |
| 6,251,132 | B1 | 6/2001 | Ravenscroft |
| 6,254,593 | B1 | 7/2001 | Wilson |
| 6,258,073 | B1 | 7/2001 | Mauch |
| 6,331,186 | B1 | 12/2001 | Wang et al. |
| 6,395,018 | B1 | 5/2002 | Castaneda |
| 6,432,129 | B2 | 8/2002 | DiCaprio et al. |
| 6,436,104 | B2 | 8/2002 | Hojeibane |
| 6,443,979 | B1 | 9/2002 | Stalker et al. |
| 6,447,501 | B1 | 9/2002 | Solar et al. |
| 6,463,317 | B1 | 10/2002 | Kucharczky et al. |
| 6,475,208 | B2 | 11/2002 | Mauch |
| 6,478,807 | B1 | 11/2002 | Foremann et al. |
| 6,488,694 | B1 | 12/2002 | Lau et al. |
| 6,494,875 | B1 | 12/2002 | Mauch |
| 6,530,947 | B1 | 3/2003 | Euteneuer et al. |
| 6,533,806 | B1 | 3/2003 | Sullivan et al. |
| 6,547,813 | B2 | 4/2003 | Stiger et al. |
| 6,562,063 | B1 | 5/2003 | Euteneuer et al. |
| 6,582,460 | B1 | 6/2003 | Cryer |
| 6,589,274 | B2 | 7/2003 | Stiger et al. |
| 6,602,226 | B1 | 8/2003 | Smith et al. |
| 6,663,665 | B2 | 12/2003 | Shaolian et al. |
| 6,676,667 | B2 | 1/2004 | Mareiro et al. |
| 6,802,849 | B2 | 10/2004 | Blaesser et al. |
| 6,802,856 | B2 | 10/2004 | Wilson |
| 6,841,213 | B2 | 1/2005 | Parsonage et al. |
| 7,001,419 | B2 | 2/2006 | DiCaprio et al. |
| 7,255,711 | B2 | 8/2007 | Holman et al. |
| 7,722,663 | B1 | 5/2010 | Austin |
| 7,998,189 | B2 | 8/2011 | Kolbel et al. |
| 8,206,427 | B1 | 6/2012 | Ryan et al. |
| 8,801,769 | B2 | 8/2014 | Chobotov |
| 9,364,314 | B2 | 6/2016 | Berra et al. |
| 2001/0023369 | A1 | 9/2001 | Chobotov |
| 2001/0037142 | A1 | 11/2001 | Stelter et al. |
| 2001/0047150 | A1 | 11/2001 | Chobotov |
| 2001/0049509 | A1 | 12/2001 | Sekine et al. |
| 2002/0052627 | A1 | 5/2002 | Boylan et al. |
| 2002/0156521 | A1 | 10/2002 | Ryan et al. |
| 2002/0183826 | A1 | 12/2002 | Dorn et al. |
| 2003/0199967 | A1 | 10/2003 | Hartley et al. |
| 2004/0044358 | A1 | 3/2004 | Khosravi et al. |
| 2004/0064083 | A1 | 4/2004 | Becker |
| 2004/0093058 | A1 | 5/2004 | Cottone et al. |
| 2004/0148008 | A1 | 7/2004 | Goodson et al. |
| 2004/0176836 | A1 | 9/2004 | Kari et al. |
| 2005/0004660 | A1 | 1/2005 | Rosenbluth et al. |
| 2005/0154443 | A1 | 7/2005 | Linder et al. |
| 2006/0079952 | A1 | 4/2006 | Kaplan et al. |
| 2007/0078506 | A1 | 4/2007 | McCormick et al. |
| 2007/0276461 | A1 | 11/2007 | Andreas et al. |
| 2008/0051705 | A1 | 2/2008 | Von Oepen et al. |
| 2008/0208240 | A1 | 8/2008 | Paz |
| 2008/0264102 | A1 | 10/2008 | Berra |
| 2008/0312671 | A1 | 12/2008 | Riles et al. |
| 2009/0082845 | A1 | 3/2009 | Chobotov |
| 2009/0125098 | A1 | 5/2009 | Chuter |
| 2009/0312830 | A1 | 12/2009 | McNulty et al. |
| 2010/0249908 | A1 | 9/2010 | Chau et al. |
| 2010/0286760 | A1 | 11/2010 | Beach et al. |
| 2011/0238160 | A1 | 9/2011 | Molony |
| 2012/0191174 | A1 | 7/2012 | Vinluan et al. |
| 2013/0261734 | A1 | 10/2013 | Young et al. |
| 2013/0268048 | A1 | 10/2013 | Watson et al. |
| 2013/0268056 | A1 | 10/2013 | Chobotov et al. |
| 2013/0268057 | A1 | 10/2013 | Vinluan et al. |
| 2013/0338753 | A1 | 12/2013 | Geusen |
| 2015/0073523 | A1 | 3/2015 | Chobotov |
| 2015/0164667 | A1 | 6/2015 | Vinluan et al. |

FOREIGN PATENT DOCUMENTS

| | | |
|---|---|---|
| EP | 1327422 | 7/2003 |
| EP | 1377234 | 1/2013 |
| EP | 2 640 319 | 9/2013 |
| EP | 2 640 319 B1 | 10/2016 |
| WO | WO 96/14808 | 5/1996 |
| WO | WO 97/17898 | 5/1997 |
| WO | WO 01/76509 | 10/2001 |
| WO | WO 04/019823 | 3/2004 |
| WO | WO 05/115275 | 12/2005 |
| WO | WO 09/132309 | 10/2009 |
| WO | WO 12/068175 | 5/2012 |
| WO | WO 16/065208 | 4/2016 |
| WO | WO 16/191602 | 12/2016 |
| WO | WO 17/019913 | 2/2017 |

OTHER PUBLICATIONS

International Search Report and Written Opinion dated Feb. 2, 2016 in International Patent Application No. PCT/US2015/057016 filed: Oct. 22, 2015 and published as: WO/2016/065208 on: Apr. 28, 2016.
International Search Report and Written Opinion dated Sep. 12, 2016 in International Patent Application No. PCT/US2016/034427 filed: May 26, 2016 and published as: WO/2016/191602 on Dec. 1, 2016.
International Search Report and Written Opinion dated Dec. 1, 2016 in International Patent Application No. PCT/US2016/044583 filed: Jul. 28, 2016 and published as: WO/2017/019913 on: Feb. 2, 2017.
International Search Report and Written Opinion dated Jun. 12, 2012 in International Patent Application No. PCT/US2011/060873 filed: Nov. 15, 2011 and published as: WO/2012/068175 on: May 24, 2012.
Extended European Search Report dated Jan. 27, 2015 in European Application No. EP 11841183.4 filed: Nov. 15, 2011.
Supplemental European Search Report dated Feb. 13, 2015 in European Application No. EP 11841183.4 filed: Nov. 15, 2011.

(56) References Cited

OTHER PUBLICATIONS

Extended European Search Report dated Dec. 13, 2018, from application No. 16800744.1.
Chinese Office Action dated Sep. 2, 2019, from application No. 201680036853.8.

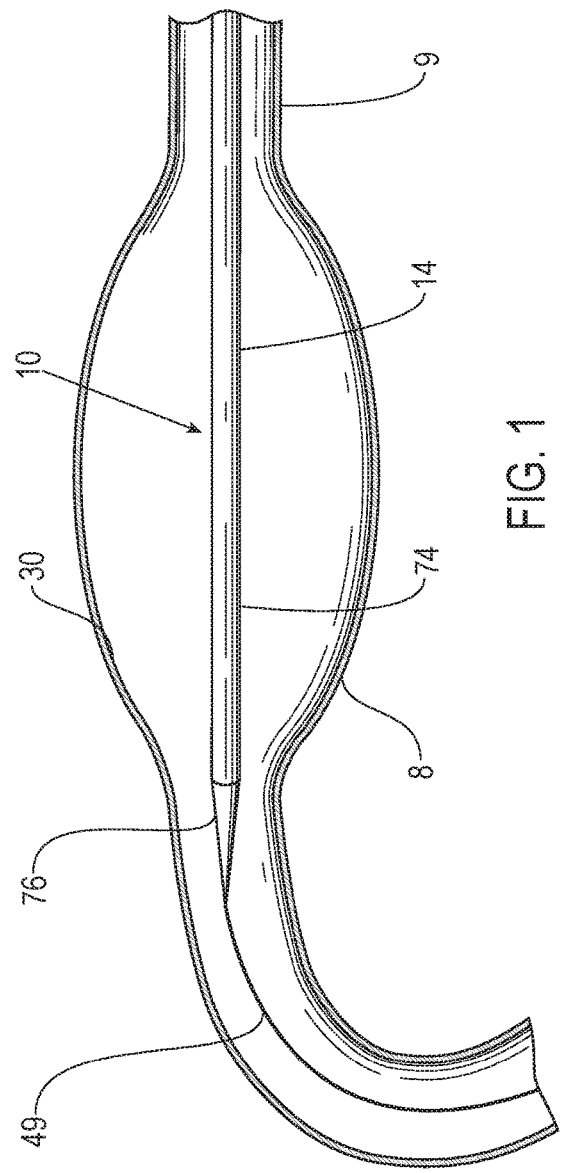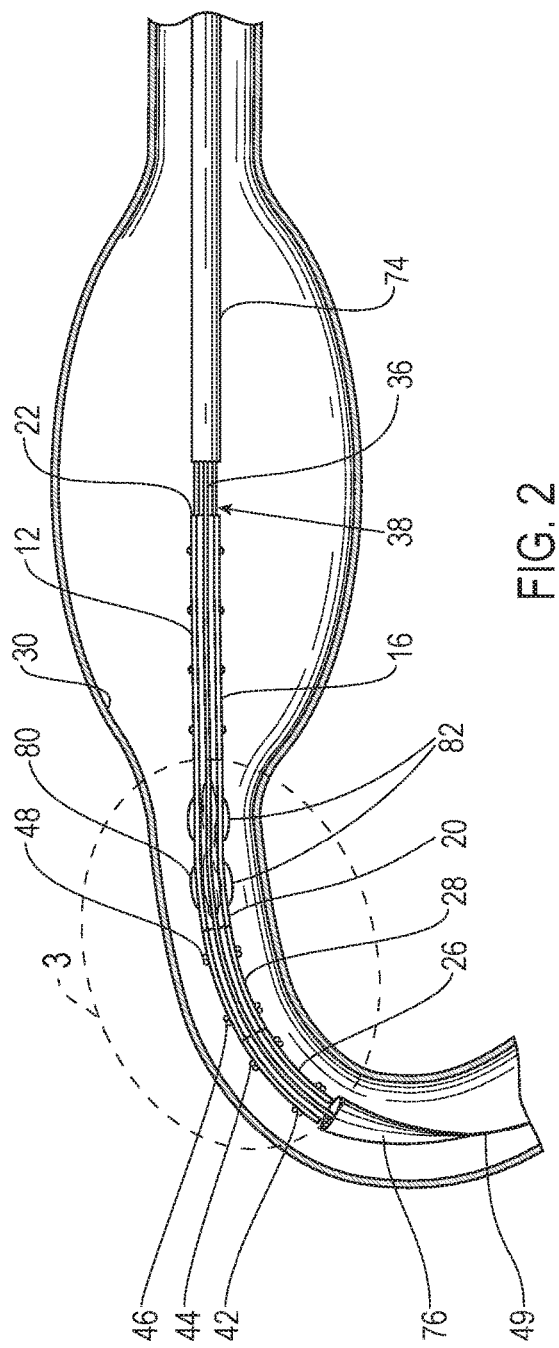
FIG. 1
FIG. 2

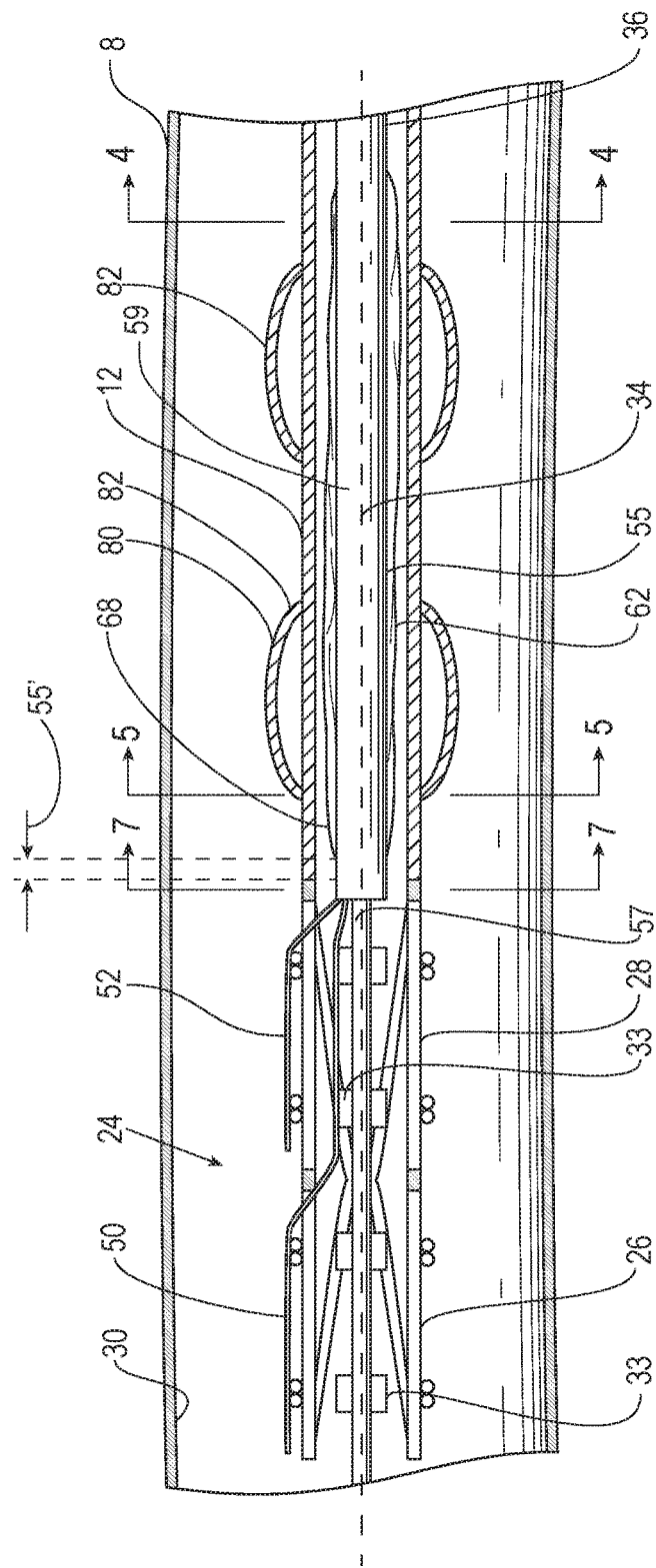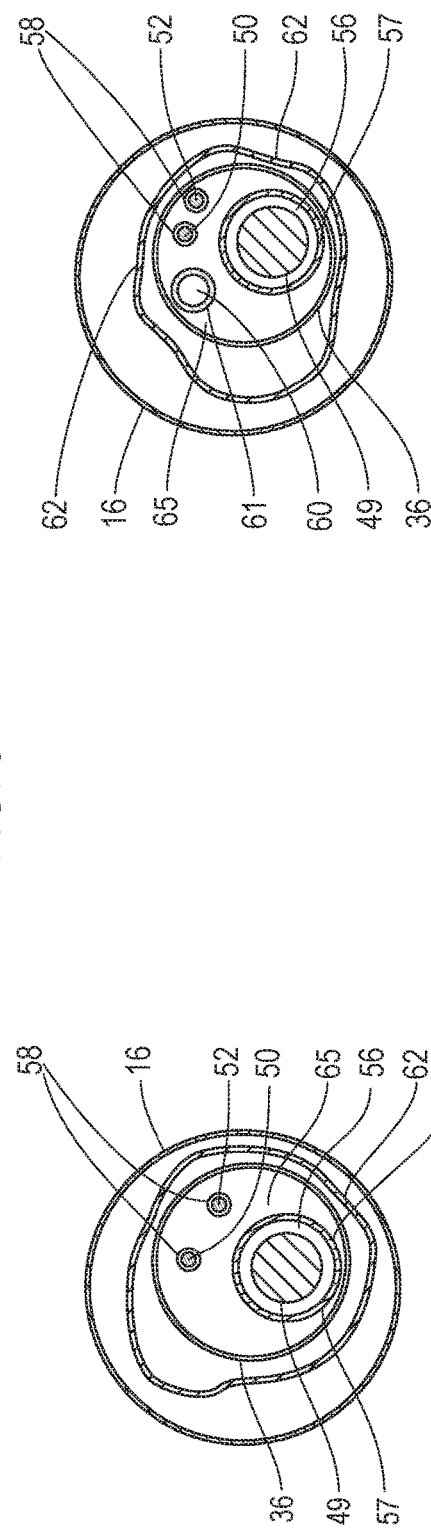
FIG. 3
FIG. 4
FIG. 5

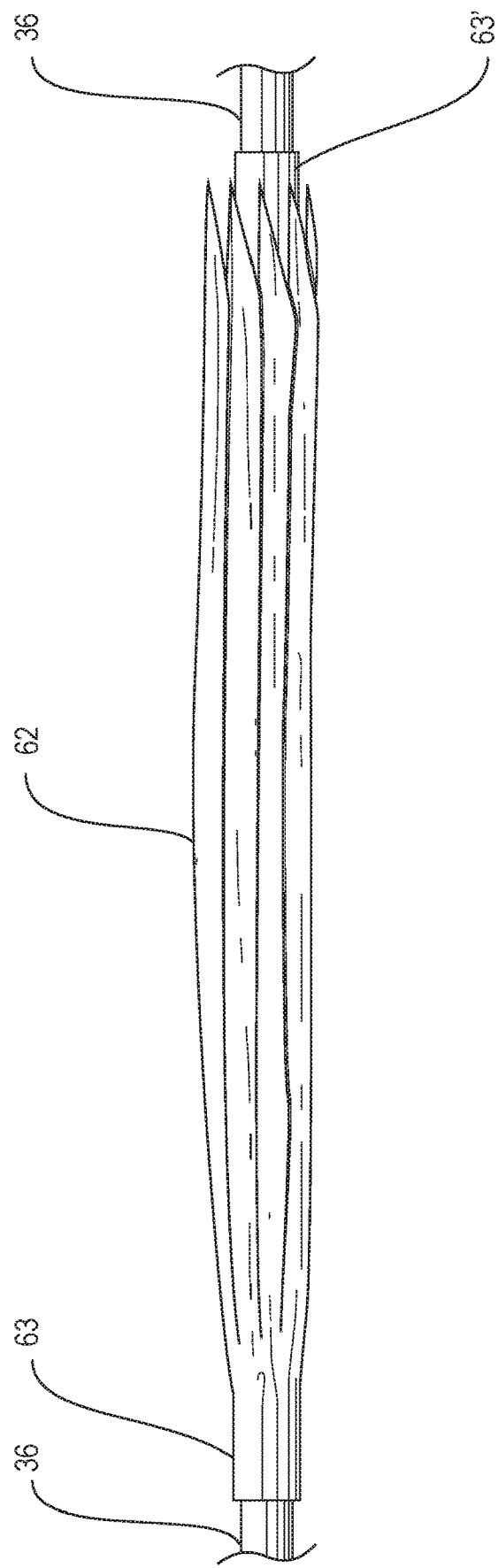

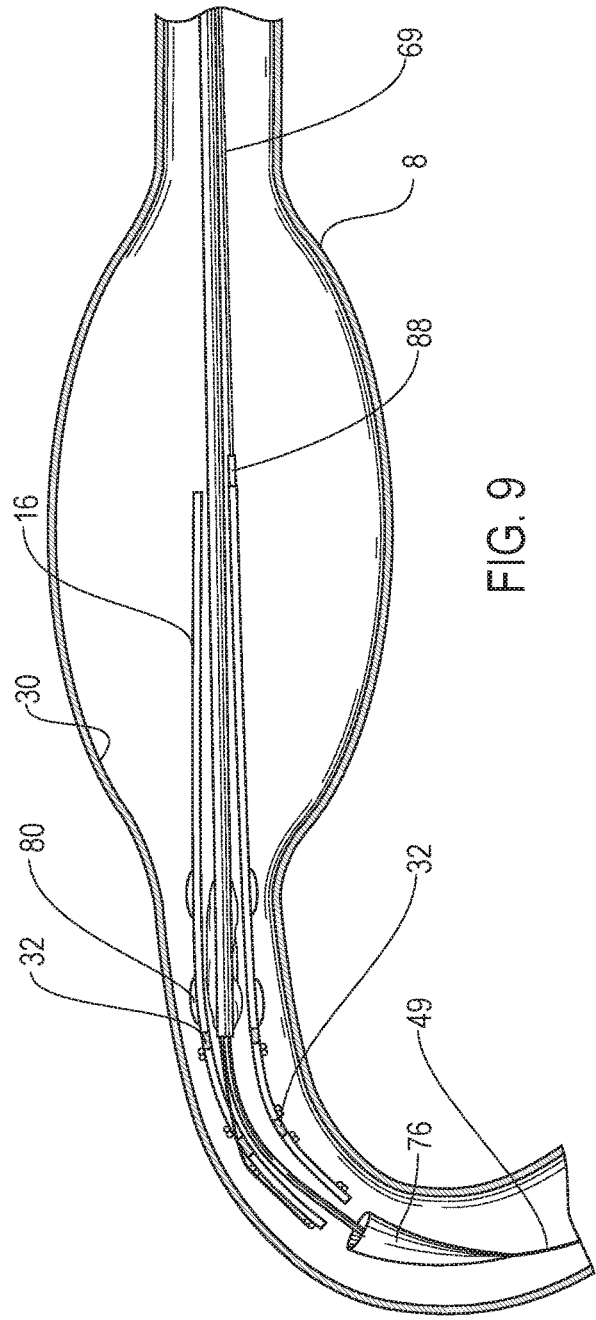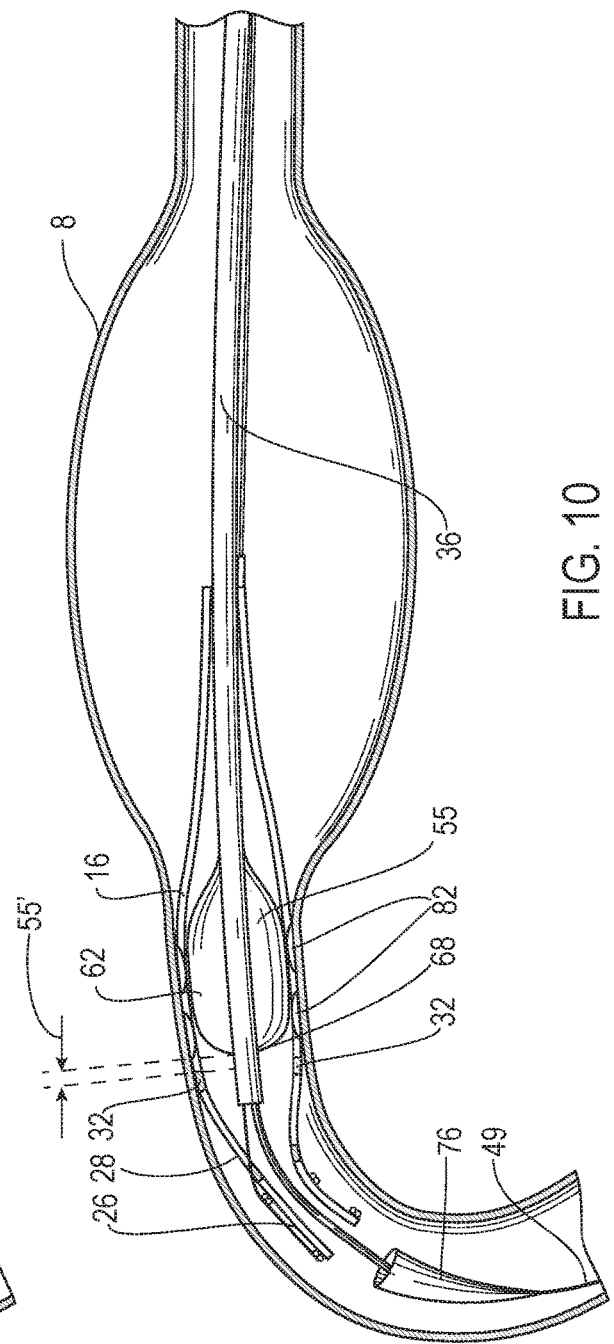

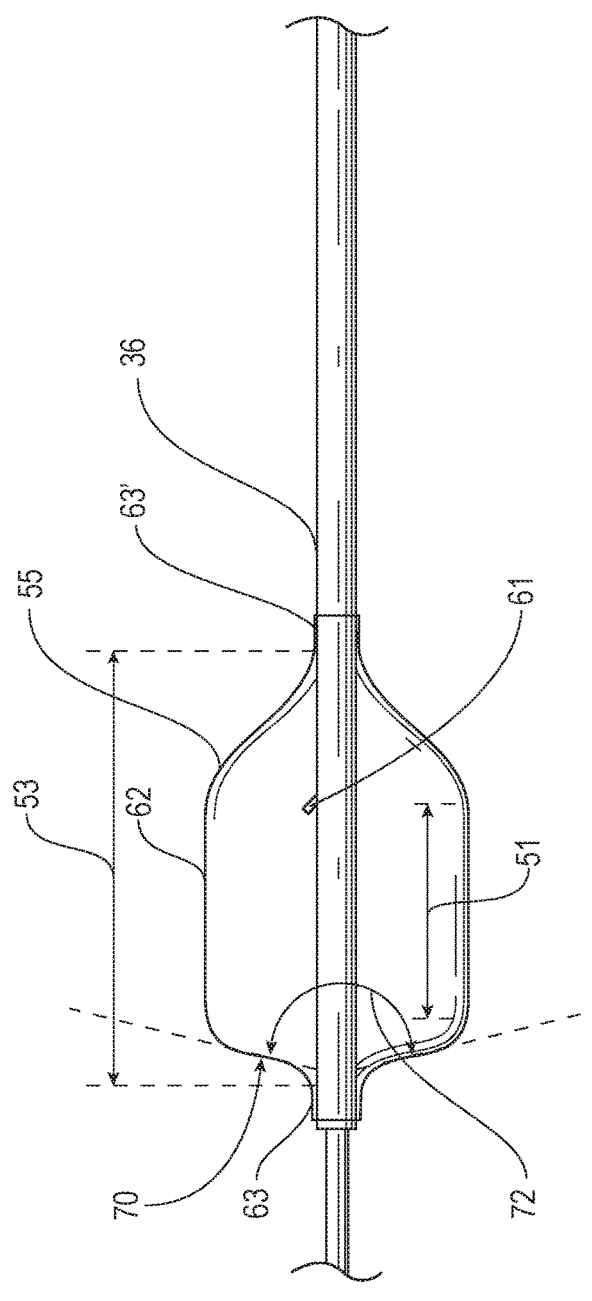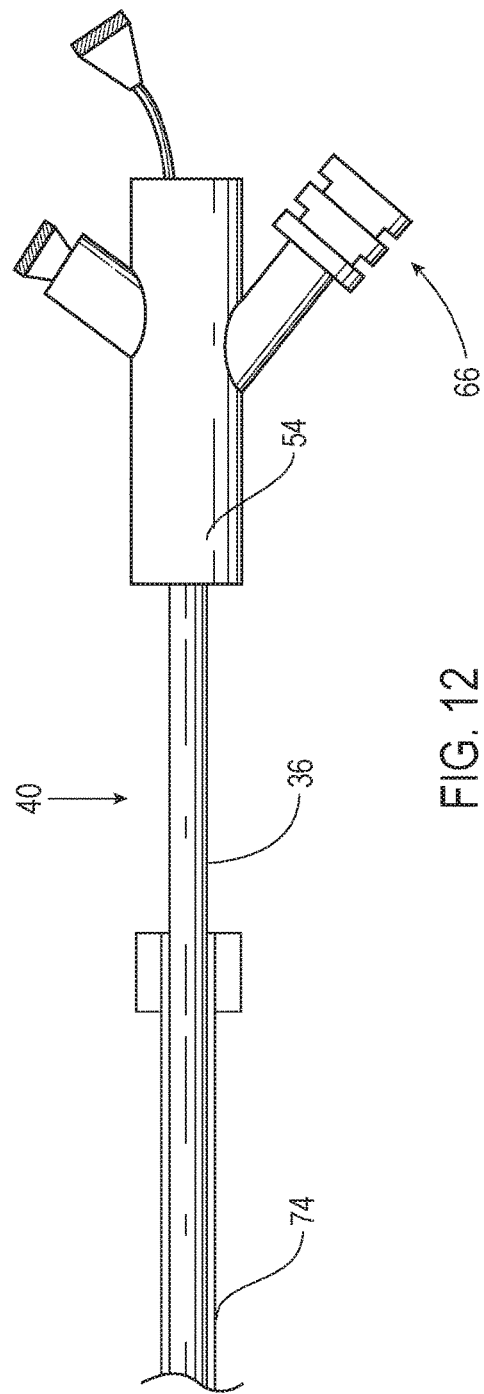

BALLOON ASSISTED ENDOLUMINAL PROSTHESIS DEPLOYMENT

RELATED PATENT APPLICATION(S)

This patent application is a national stage application under 35 U.S.C. section 371 of International Patent Application No. PCT/US2016/034427, filed May 26, 2016, naming Mark Geusen as inventor, entitled BALLOON ASSISTED ENDOLUMINAL PROSTHESIS DEPLOYMENT, which claims the benefit of U.S. provisional patent application No. 62/167,247, filed May 27, 2015, naming Mark Geusen as inventor, entitled BALLOON ASSISTED ENDOLUMINAL PROSTHESIS DEPLOYMENT, the entirety of each of which is incorporated by reference herein, including all text and drawings.

BACKGROUND

An aneurysm is a vascular defect indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of an AAA is described in a book titled Surgical Treatment of Aortic Aneurysms by Denton A. Cooley, M. D., published in 1986 by W. B. Saunders Company.

Due to the inherent risks and complexities of surgical repair of aortic aneurysms, minimally invasive endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989).

When deploying endoluminal prosthesis type devices by catheter or other suitable instrument, it may be advantageous to have a flexible and low profile endoluminal prosthesis such as a stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process, particularly for use in treatment of vascular defect sites that include a high degree of curvature or angulation. Even with more flexible low profile delivery systems, deployment of endovascular prostheses in highly angulated and curved vessels may be problematic due to difficulties with visualization or imaging of the orientation of the prostheses during the deployment process. Achieving a proper seal between an outer surface of an endovascular prosthesis and an inner surface of a vessel being treated after deployment of the endovascular prosthesis may also be challenging in some instances. As such, minimally invasive endovascular treatment of aneurysms may not be available for many patients that would benefit from such a procedure and can be more difficult to carry out for those patients for whom the procedure is indicated.

What have been needed are endoluminal prostheses and suitable delivery catheters that are adaptable to a wide range of patient anatomies and that can be safely and reliably deployed using a flexible low profile system.

SUMMARY

Some embodiments of a delivery system for treatment of a vascular defect may include an endoluminal prosthesis for treatment of the vascular defect and a delivery catheter. The endoluminal prosthesis may include a tubular main graft portion with a thin flexible material, a main inner lumen, a proximal end and a distal end. The endoluminal prosthesis may also have a self-expanding anchor member that has a proximal portion and a distal portion. A distal end of the distal portion may be secured to a proximal end of the tubular main graft portion and a distal end of the proximal portion may be secured to a proximal end of the distal portion. In addition, the endoluminal prosthesis may also have a plurality of radiopaque markers which are circumferentially disposed adjacent the proximal end of the tubular main graft portion. For some embodiments, the delivery catheter of the delivery system may include an elongate shaft with sufficient column strength for percutaneous advancement within a patient's vasculature, the elongate shaft also having a proximal section and a distal section. A plurality of releasable belts may be disposed on the proximal section of the elongate shaft and configured to releasably constrain the self-expanding anchor member of the endoluminal prosthesis. A plurality of elongate release members may be disposed in operative communication with a distal end of the elongate shaft and said elongate release members may each include a proximal section configured to releasably secure at least one respective releasable belt while said releasable belt is in a configuration that constrains at least a portion of the self-expanding anchor member of the endoluminal prosthesis. An inflatable balloon may be secured to the elongate shaft within the main inner lumen of the tubular main graft portion of the endoluminal prosthesis. In some instances, the inflatable balloon may be disposed in an axial position wherein a proximal end of an inflatable section of the inflatable balloon is positioned adjacent but distal of the self-expanding anchor member. In some instances, the inflatable balloon may be disposed in an axial position wherein a proximal end of an inflatable section of the inflatable balloon is positioned adjacent but distal of the radiopaque markers. For some inflatable balloon embodiments, a proximal neck portion (a portion of a tubular member of the inflatable balloon tube which is in contact with an outer surface of the shaft) of some inflatable balloon embodiments may be positioned proximal the radiopaque markers so long as the proximal angled portion or proximal cone of the inflatable balloon and any pleats of the inflatable balloon material are disposed distal to the radiopaque markers.

Some embodiments of a method of deploying an endoluminal prosthesis may include advancing a delivery system into a patient's vasculature which includes an elongate shaft and an endoluminal prosthesis releasably secured to the elongate shaft. The method may also include releasing an outer constraint from a main graft portion of the endoluminal prosthesis and partially releasing an outer radial constraint from a self-expanding anchor member of the endoluminal prosthesis to allow the self-expanding anchor member to partially deploy. Thereafter, an inflatable balloon may be inflated and radially expanded so as to radially expand a portion of a graft portion of the endoluminal prosthesis which is disposed adjacent and axially coextensive with the inflatable balloon. In some cases, the inflatable balloon may be disposed within a main inner lumen of the main graft portion of the endoluminal prosthesis with a proximal end of an inflatable section of the inflatable balloon being disposed adjacent but distal of the self-expanding anchor member. In some cases, the inflatable balloon may be disposed within a main inner lumen of the main graft portion of the endoluminal prosthesis with a proximal end of an inflatable section of the inflatable balloon being disposed adjacent but distal of a plurality of radiopaque markers which may be circumferentially disposed adjacent a proximal edge of the main graft portion of the endoluminal prosthesis. An outer radial constraint on the self-expanding anchor member may then be fully released so as to fully deploying the self-expanding anchor member of the endoluminal prosthesis. In some cases, inflating and radially expanding the inflatable balloon may include inflating and radially expanding the inflatable balloon so as to apply an outward radial force onto an inner surface of a main inner lumen of the main graft portion of the endoluminal prosthesis until an outer surface of the main graft portion adjacent the inflatable balloon is urged into contact with an inner surface of the patient's vasculature.

Some embodiments of a delivery system for treatment of a vascular defect may include an endoluminal prosthesis for treatment of the vascular defect including and a delivery catheter. The endoluminal prosthesis may include a tubular main graft portion having a thin flexible material, a main inner lumen, a proximal end and a distal end. The endoluminal prosthesis may also include a self-expanding anchor member with a distal end thereof being secured to the proximal end of the tubular main graft portion. The delivery catheter may include an elongate shaft having a distal section and a proximal section, the proximal section being configured to releasably secure the endoluminal prosthesis in a constrained state. The delivery catheter may also include an inflatable balloon secured to the elongate shaft and disposed within the main inner lumen of the tubular main graft portion of the endoluminal prosthesis in an axial position wherein a proximal end of an inflatable section of the inflatable balloon is disposed adjacent but distal of the self-expanding anchor member.

BRIEF DESCRIPTION OF THE DRAWINGS

FIG. 1 is an elevation view in partial section of a delivery system embodiment being advanced over a guidewire into an aorta of a patient's vasculature.

FIG. 2 is an elevation view of the delivery system embodiment of FIG. 1 with an outer sheath of a delivery catheter of the delivery system embodiment retracted.

FIG. 3 is an enlarged view of a proximal portion of the delivery system embodiment of FIG. 2 as indicated by the encircled portion 3-3 in FIG. 2.

FIG. 4 is a transverse cross section view of the delivery system embodiment of FIG. 3 taken along lines 4-4 in FIG. 3.

FIG. 5 is a transverse cross section view of the delivery system embodiment of FIG. 3 taken along lines 5-5 in FIG. 3.

FIG. 6 is an elevation view of a pleated embodiment of an inflatable balloon.

FIG. 9 is an elevation view of the delivery system embodiment of FIG. 1 with the self-expanding anchor member partially deployed wherein an outer radial constraint on the distal portion of the self-expanding anchor member has been removed.

FIG. 10 is an elevation view of the delivery system embodiment of FIG. 9 wherein the inflatable balloon disposed within the main inner lumen of the graft portion of the endoluminal prosthesis has been inflated.

FIG. 11 is an elevation view of an embodiment of the inflatable balloon of the delivery system embodiment of FIG. 1 in an inflated state and showing a cone angle of the proximal end surface of the inflatable balloon embodiment.

FIG. 12 is an elevation view of a distal adapter assembly and a distal portion of the delivery catheter of the delivery system embodiment of FIG. 1.

Figure 1A:
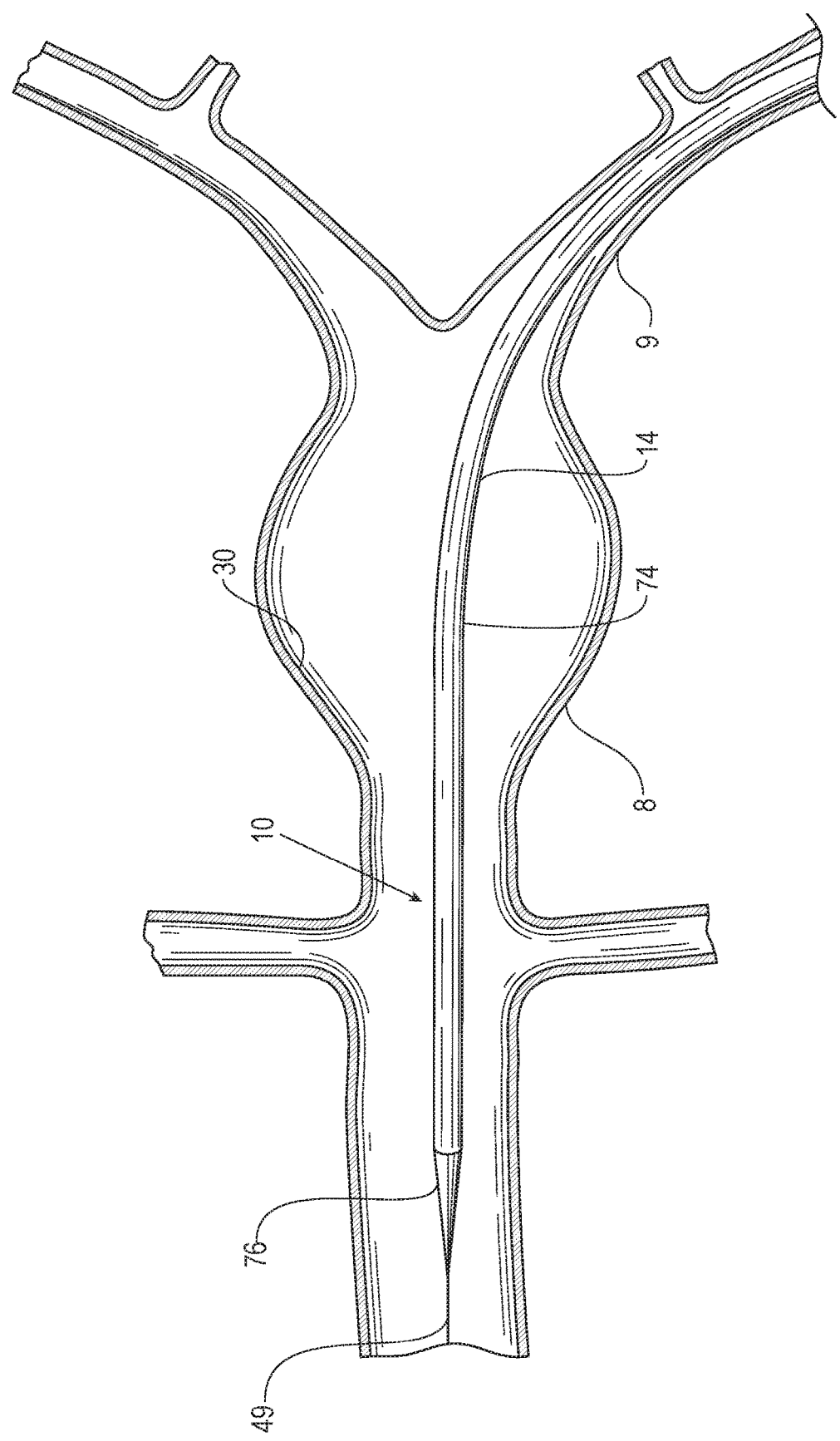
FIG. 1A is an elevation view in partial section of the delivery system of FIG. 1 being advanced over a guidewire into an abdominal aorta of a patient's vasculature.
Figure 8:
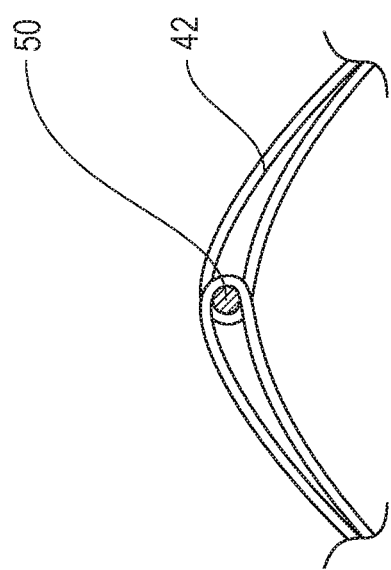
FIG. 8 is an enlarged view of a release wire embodiment disposed within end loops of releasable belt embodiments of the delivery catheter of the delivery system embodiment of FIG. 3.
Figure 7:
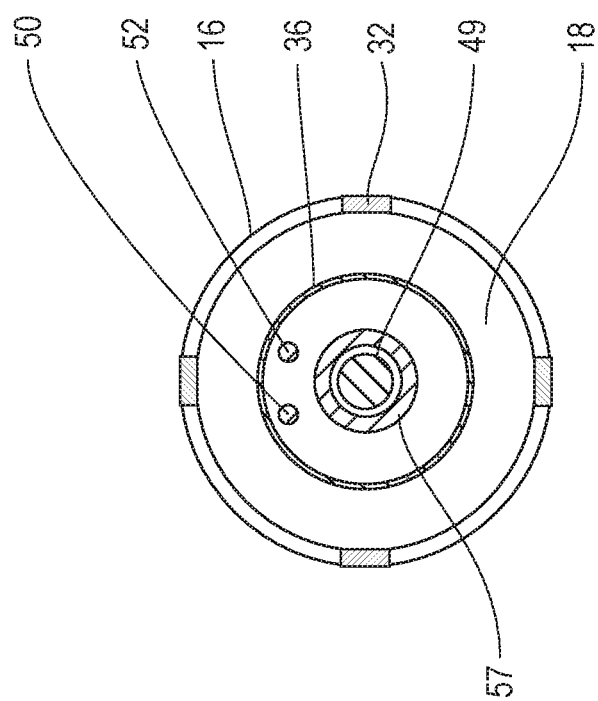
FIG. 7 is a transverse cross section view of the delivery system embodiment of FIG. 3 taken along lines 7-7 in FIG. 3.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DETAILED DESCRIPTION

As discussed above, there has been a need for endoluminal prosthesis delivery systems with a small flexible delivery profile. It may also be useful for such delivery systems to be configured to reliably open a portion of an endoluminal prosthesis that includes radiopaque markers so as to visualize the endoluminal prosthesis for proper placement under fluoroscopic imaging or the like. Embodiments discussed herein may include inflatable devices such as inflatable balloons that may be used to apply an outward radial force to an inside surface of an endoluminal prosthesis at a particular axial position during the deployment process in order to achieve these objectives. Such an inflatable balloon disposed within a graft portion of an endoluminal prosthesis that includes a self-expanding anchor member may be useful in improving the opening and deployment of the prosthesis. The improved deployment may be particularly useful in angulated vessels 9 of a patient being treated. Such an inflatable balloon component may also be useful to help seal an outer surface of an endoluminal prosthesis to an inner surface of a lumen being treated.

With regard to the delivery system embodiments discussed herein, including the endoluminal prostheses, delivery catheter embodiments and associated structures and methods, the term "proximal" refers to a location towards a patient's heart and away from an operator who is using the delivery system to deploy an endoluminal prosthesis. The term "distal" refers to a location away from the patient's heart and towards the operator.

Referring to the figures, an embodiment of a delivery system 10 for treatment of a vascular defect such as aneurysm 8 is shown in FIGS. 1-12. Although the exemplary aneurysm 8 shown in the patient's vasculature 9 is a thoracic type aortic aneurysm, devices and methods as discussed herein and illustrated in the corresponding figures may also be used for any other suitable type of vascular defect such as abdominal aortic aneurysms (shown in FIG. 1A) and the like. The delivery system embodiment 10 may include an endoluminal prosthesis 12 for treatment of the vascular defect 8 and a delivery catheter 14. The endoluminal prosthesis may include a tubular main graft portion 16 made from a thin flexible material, and including a main inner lumen 18, a proximal end 20 and a distal end 22. The graft body may be formed from a flexible and supple graft material, such as PTFE, and have a main fluid flow lumen disposed in a main graft portion therein. For some embodiments, flexible graft material including PTFE may include expanded PTFE or ePTFE.

Referring to FIG. 3, the endoluminal prosthesis 12 may also have a self-expanding anchor member 24 that has a proximal portion 26 and a distal portion 28 with a distal end of the distal portion being secured to a proximal end 20 of the tubular main graft portion and a distal end of the proximal portion being secured to a proximal end of the distal portion. The self-expanding anchor member embodiment 24 shown in FIG. 2 has a generally cylindrical configuration with a free unsecured end at a proximal end thereof and a distal end that is secured to a proximal end of the main graft body. The proximal portion 26 of the self-expanding anchor member 24 may include a cylindrical stent including an elongate superelastic element disposed in a zig-zag configuration and the distal portion of the self-expanding anchor member comprises a cylindrical stent including an elongate superelastic element disposed in a zig-zag configuration. An optional connector ring (not shown) may be embedded into the structure of the proximal end of the main graft portion and may be coupled to the distal end of the proximal self-expanding anchor member 24. In some cases, such a connector ring may include a self-expanding zig-zag shaped made from a superelastic material such as a nickel titanium alloy. The deployment assistance provided by the inflatable balloon due to the outward radial force supplied by the inflatable balloon may be particularly useful in endoluminal prosthesis embodiments that do not include a self-expanding connector ring. In some cases such a connector ring may be useful to provide an opening force at the proximal end of the graft portion of the endoluminal prosthesis during deployment.

In some instances the proximal self-expanding anchor member 24, including a proximal portion and distal portion thereof, may have a monolithic structure with the proximal portion and distal portion both formed from a single piece of continuous material with no joints formed between the portions. In some cases, embodiments of the self-expanding anchor member 24 may be made from a superelastic metal, including superelastic metals such as nickel titanium alloys.

The proximal self-expanding anchor member 24 may include outwardly extending barbs (not shown), that may be integrally formed with struts of the stent structure of either or both the proximal portion 26 and distal portion 28 of the self-expanding anchor member 24. Such barbs may have sharp or sharpened tissue penetrating tips configured to penetrate into tissue of an inside surface 30 of a lumen within which the proximal self-expanding anchor member 24 may be deployed in an expanded state. Such a barb configuration may be used to facilitate securement of the self-expanding anchor member 24 to the inner surface 30 of the patient's vasculature 9 or other luminal surface.

Although the self-expanding anchor members discussed herein may include a proximal portion and a distal portion, other embodiments may be used. In addition, similar expanding anchor members may be used that are configured to be inelastically expanded with outward radial pressure as might be generated by the expansion of a radially expandable inflatable balloon from within either or both the proximal portion and distal portion of the proximal self-expanding anchor member. Such inelastically expandable anchor members may otherwise have the same features, dimensions and configurations as those of the self-expanding anchor members discussed herein.

In addition, the endoluminal prosthesis 12 may also have a plurality of radiopaque markers 32 which are circumferentially disposed about a tubular configuration of the endoluminal prosthesis 12 adjacent the proximal end 20 of the tubular main graft portion. In some cases, the plurality of radiopaque markers 32 may be substantially equally spaced around a circumference of a tubular portion of the endoluminal prosthesis 12 and all lie in a common plane which is substantially perpendicular to a longitudinal axis 34 of the proximal self-expanding anchor member and main graft portion of the endoluminal prosthesis 24. In some cases, the radiopaque markers 32 may be disposed around a circumference of the self-expanding anchor member 24 at a distal end of the self-expanding anchor member 24. Such an arrangement may be useful in visualizing the alignment of the endoluminal prosthesis during the deployment process. Some endoluminal prosthesis embodiments may include about 4 to about 12, more specifically, about 5 to about 8, such circumferentially spaced radiopaque markers 32 lying in a common plane, the common plane optionally being perpendicular to a longitudinal axis 34 of the main graft portion of the endoluminal prosthesis.

For some embodiments, the delivery catheter 14 of the delivery system 10 may include an elongate shaft 36 with sufficient column strength for percutaneous advancement within a patient's vasculature 8, the elongate shaft 36 also having a proximal section 38 and a distal section 40. A plurality of releasable belts may be disposed on the proximal section 38 of the elongate shaft 36 and configured to releasably constrain a self-expanding anchor member of an endoluminal prosthesis. A plurality of appropriately sized cylindrical bushings or pads 33 may be secured over the elongate shaft adjacent one or more of the releasable belts in order to properly space the self-expanding anchor member 24 or portions thereof while in a constrained state. A plurality of elongate release members may be disposed in operative communication with a distal section of the elongate shaft 36 and said elongate release members may each include a proximal section configured to releasably secure at least one respective releasable belt while said releasable belt is in a configuration that constrains at least a portion of the self-expanding anchor member 24 of the endoluminal prosthesis 12.

The plurality of releasable belts configured to releasably constrain the proximal self-expanding anchor member 24 of the endoluminal prosthesis 10 may be secured along the proximal section 38 of the elongate shaft 36. Referring to FIG. 2, a first proximal releasable belt 42 and second proximal releasable belt 44 are secured about the proximal portion 26 of the self-expanding anchor member 24. A first distal releasable belt 46 and second distal releasable belt 48 are secured about the distal portion 28 of the self-expanding anchor member 24.

Referring to FIG. 3, at least a first elongate release member 50 and second elongate release member 52, which may include elongate release wires for some embodiments, may extend to and be in communication with a distal end of the elongate shaft 36. For some embodiments, three or more release wires may be used. For some embodiments, an additional release wire (not shown) may be used to provide a releasable interlock for a connection or coupling between a fill tube 69 and inflatable portion of an inflatable embodiment of the endoluminal prosthesis 12. The first release member 50 and second release member 52 may have a proximal section configured to releasably secure at least one respective releasable belt, such as the first proximal releasable belt 42, second proximal releasable belt 44, first distal releasable belt 46, or second distal releasable belt 48, while the releasable belts are in a configuration that constrains at least a portion of the endoluminal prosthesis 10, such as the proximal self-expanding anchor member 24. The release members 50, 52 may be configured to deploy the self-expanding anchor member 24 at a proximal end of the endoluminal prosthesis 12.

Referring to FIGS. 2 and 3, a first release wire 50 shown is coupled to the first proximal releasable belt 42 and the second proximal releasable belt 44 and can thereby be used to deploy the first proximal releasable belt 42 and second proximal releasable belt 44 (in that order) by distally retracting the first release member 50 by a mechanism in a distal adapter 54 (shown in FIG. 12) or any other suitable method. The second release member 52 shown is coupled to the first distal releasable belt 46 and the second distal releasable belt 48 and can thereby be used to deploy the first distal releasable belt 46 and second distal releasable belt 48 (in that order) by distally retracting the second release member 52 by a mechanism in a distal adapter 54 or any other suitable method.

In some instances, the friction generated by axial movement of the first and second release members 50, 52 may be minimized by using a multi-lumen configuration in the elongate shaft 36 of the delivery catheter 14. Such a delivery catheter embodiment 14 may include an elongate shaft 36 with one or more release member lumens 58 extending within a release member sleeve 67, a guidewire lumen 56 extending within a guidewire tube 57 for passage of a guidewire 49, an inflation lumen 60 for inflation of an inflatable balloon 62 extending within an inflation tube 61 and an optional fill lumen 64 for filling an optional inflatable portion of the endoluminal prosthesis 12 extending within a fill tube 69. The section of the elongate shaft 36 of the delivery catheter embodiment 14 shown in FIG. 5 illustrates the release member lumens 58 and guidewire lumen 56, surrounded by guidewire tube 57. The section in FIG. 4 also includes the inflation lumen 60 surrounded by the inflation tube 61.

For some embodiments, the inflation tube 61 may have an inflation lumen 60 with a substantially round inner transverse section, for other embodiments, the inflation lumen 60 may have a transverse section that is oval in shape. In some cases, the round inflation lumen embodiments may have an inner diameter of about 0.01 inches to about 0.03 inches, more specifically, about 0.014 inches to about 0.016 inches, 0.01 inches to about 0.02 inches, 0.02 inches to about 0.025 inches, about 0.015 inches, or any other suitable inner diameter. Some oval inflation lumen embodiments 60 may have a major inner transverse dimension of about 0.055 inches to about 0.060 inches, and a minor inner transverse dimension of about 0.024 inches to about 0.028 inches. Inflation tube lumen embodiments 61A, 61A' and 61A" shown in FIGS. 27-33 are configured to accommodate respective inflation tubes 61 and 61'. Each of these lumen embodiments 56, 58, 60 and 64 and tube or sleeve embodiments 57, 61, 67 and 69 may extend axially along or within the elongate shaft 36 of the delivery catheter 14 from a proximal section to a distal end thereof, including to the distal adapter 54 at the distal end of the elongate shaft 36. In some cases, the release members may be coupled to respective deployment knobs 66 disposed on the distal adapter 54 shown in FIG. 12.

The inflatable balloon 62 which may be integrally formed with the elongate shaft 36 may be operatively secured to the elongate shaft 36 of the delivery catheter 14 within the main inner lumen 18 (shown in FIG. 7) of the tubular main graft portion 16 of the endoluminal prosthesis 12. In some instances, the inflatable balloon 62 may be disposed in an axial position wherein a proximal end 68 of an inflatable section 55 of the inflatable balloon 62 is positioned adjacent but distal of the radiopaque markers 32. In some cases, the inflatable balloon 62 may be disposed within a non-deployed constrained endoluminal prosthesis 12 in an axial position with the proximal end 68 of the inflatable section 55 of the inflatable balloon 62 disposed adjacent but distal of the self-expanding anchor member structure such as a self-expanding anchor member 24 as shown in FIGS. 3, 9 and 10. The inflatable section 55 of the inflatable balloon 62 may also be disposed with a proximal end 68 of the inflatable section 55 thereof disposed adjacent but distally of any other high strength resilient structures that may be associated with securing an anchor member portion of an endoluminal prosthesis 12 to a main graft portion 16 of an endoluminal prosthesis 12, such as a connector ring. In addition, in some cases the inflatable section 55 of the inflatable balloon 62 may be axially positioned so as to fail to axially overlap or lie in the same horizontal plane as the self-expanding anchor member 24 or any other high strength structure associated with the self-expanding anchor member 24.

Figure 23:
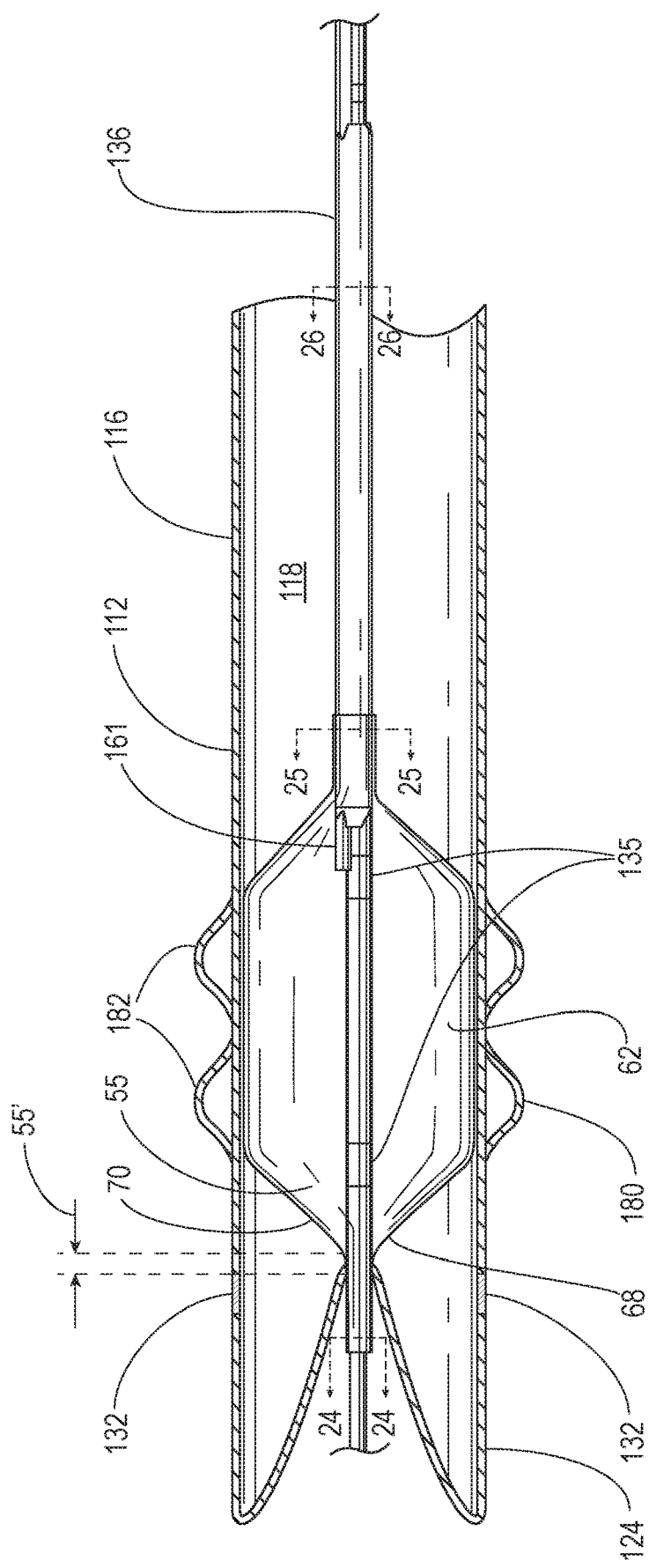
FIG. 23 is an elevation view of an inflatable balloon portion embodiment of the delivery system of FIG. 15.
Figure 26:
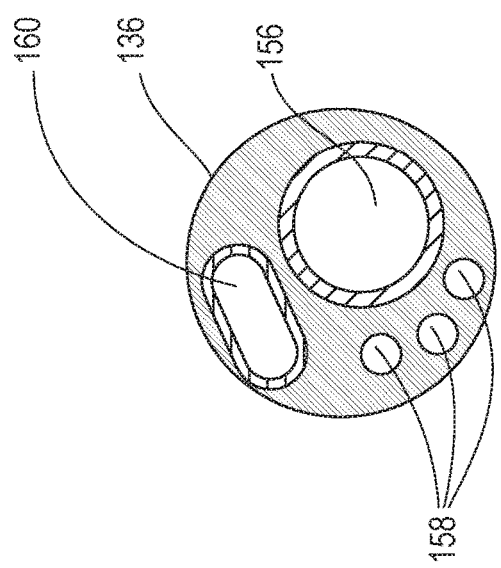
FIG. 26 is a transverse cross section of the inflatable balloon portion of FIG. 23 taken along lines 26-26.
Figure 25:
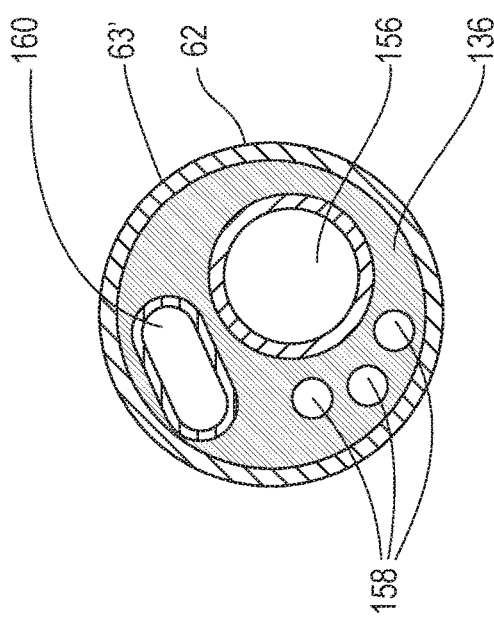
FIG. 25 is a transverse cross section of the inflatable balloon portion of FIG. 23 taken along lines 25-25.
Figure 24:
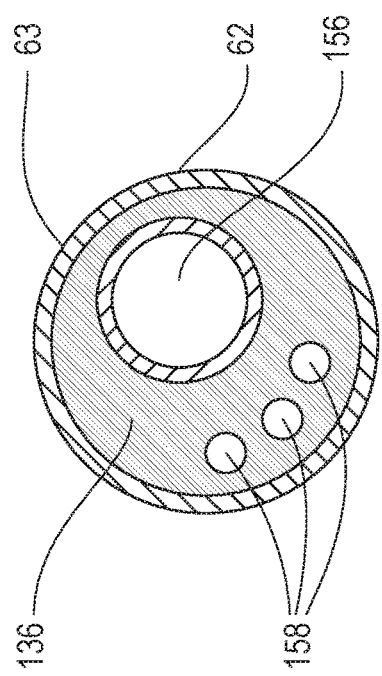
FIG. 24 is a transverse cross section of the inflatable balloon portion of FIG. 23 taken along lines 24-24.
Figure 27:
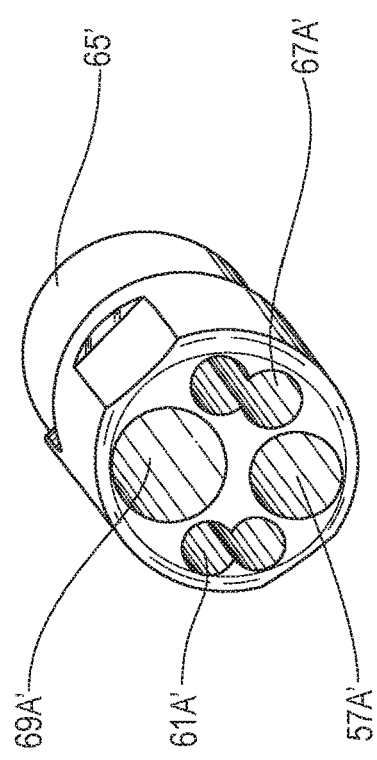
FIG. 27 is a perspective view of an embodiment of a multi-lumen member for a multi-lumen delivery catheter embodiment.
Figure 28:
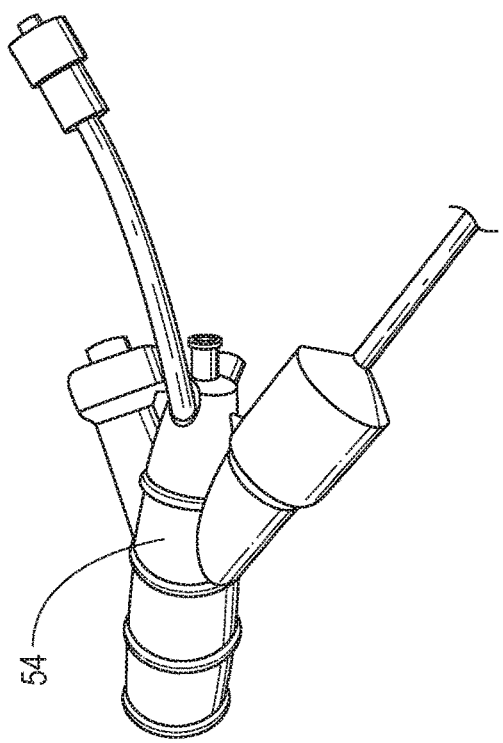
FIG. 28 is a perspective view of an embodiment of a multi-lumen member for a multi-lumen delivery catheter embodiment.
Figure 29:
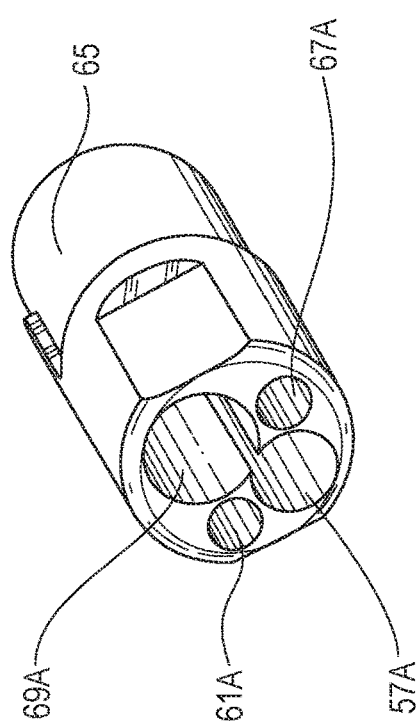
FIG. 29 is a perspective view of an embodiment of the multi-lumen member embodiment of FIG. 28.
Figure 30:
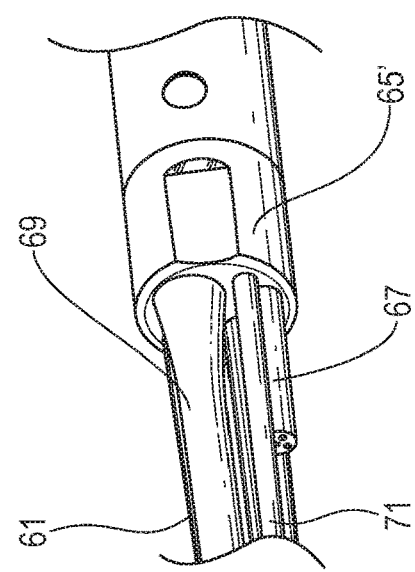
FIG. 30 is a perspective view of an embodiment of a distal adapter with a crossover port at the bottom, an inflation port for an inflatable balloon at the top and a fill port for an optional inflatable portion of an endoluminal prosthesis at the side of the adapter.
Figure 32:
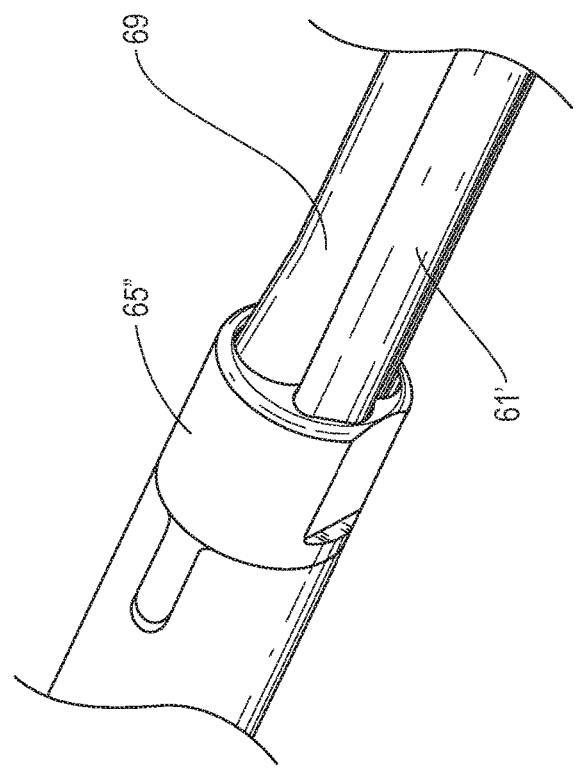
FIG. 32 is a perspective view of the multi-lumen member of FIG. 31.
Figure 31:
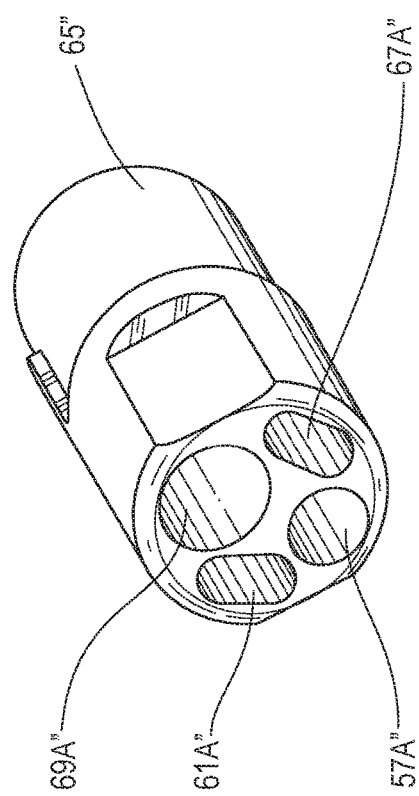
FIG. 31 is a perspective view of an embodiment of a multi-lumen member.
Figure 33:
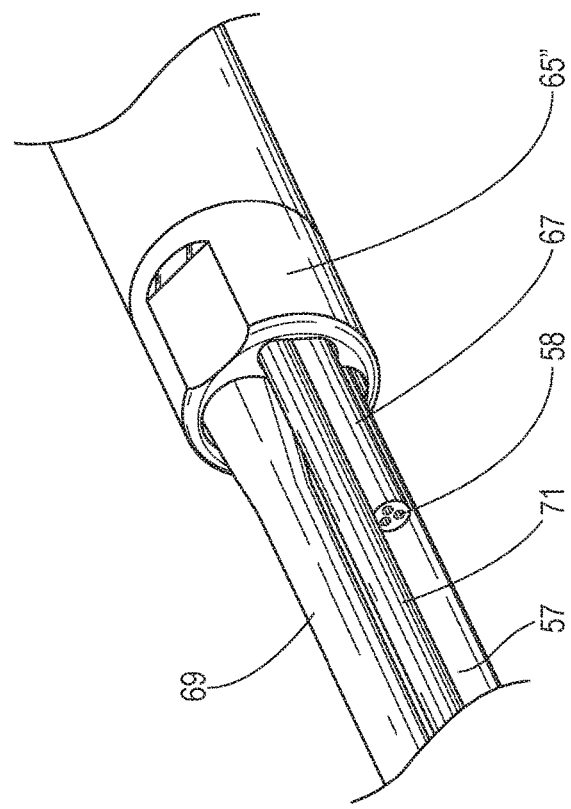
FIG. 33 is a perspective view of the multi-lumen member of FIG. 31.

With regard to the relative axial positioning of the inflatable balloon 62, the proximal end 68 of the inflatable section 55 of the inflatable balloon 62 may be said to be adjacent but distal of a structure such as the radiopaque markers 32 or self-expanding anchor member 24 if an optional axial gap between these respective elements is up to about 5 mm, more specifically, up to about 2 mm, for some embodiments. FIGS. 3, 10 and 23 (discussed below) show an example of such an optional axial gap as indicated by arrows 55'. FIGS. 3 and 10 illustrate the optional axial gap between the proximal end 68 of the inflatable section 55 of the inflatable balloon 62 and a distal most portion of the radiopaque markers 32. For the embodiment of FIG. 23, the radiopaque markers 132 overlap the structure of the distal end of the self-expanding anchor member 124. As such, FIG. 23 illustrates an optional gap 55' disposed between the proximal end of the inflatable section 55 of the inflatable balloon 62 and a distal most end of both the radiopaque markers 132 and distal most end of the self-expanding anchor member 124.

For some embodiments, the shaped tubular wall material of the inflatable balloon 62 may be secured or bonded to the elongate shaft 36 in a neck portion by adhesive such as ultraviolet cured adhesives, laser bonding or welding, thermal bonding or welding, or any other suitable method. For some embodiments, it may be desirable in order to achieve a high burst strength of the inflatable balloon 62 to use a material for the inflatable balloon 62 that is the same as or similar to a material of a balloon shaft section 59 of the elongate shaft 36 to facilitate thermal bonding, welding or the like between these two elements. The balloon shaft section 59 of the elongate shaft 36 may include a substantially tubular portion of the elongate shaft 36 extending axially within the inflatable balloon 62 and include an outer surface suitable for bonding of the balloon 62 and providing a fluid tight barrier for the interior volume of the inflatable balloon 62. With regard to material selection, some embodiments may include a balloon shaft section 59 and inflatable balloon 62 which are both made from polyurethane. For some inflatable balloon embodiments 62, a proximal neck portion 63 of some inflatable balloon embodiments 62 may be positioned proximal the radiopaque markers 32 and/or self-expanding anchor member 24 so long as the proximal angled portion or proximal cone of the inflatable balloon 62 and any pleats of the inflatable balloon 62 are disposed distal to the radiopaque markers 32 and/or self-expanding anchor member 24. The proximal neck portion 63 is a portion of a tubular member of the inflatable balloon 62 which is in contact with an outer surface of the elongate shaft 36 and typically is where the proximal end of the inflatable balloon 62 is bonded to the elongate shaft 36. The distal end of the inflatable balloon 62 is similarly bonded to the elongate shaft 36 over a distal neck portion 63'. These bonded portions 63 and 63' may have a length that is selected to provide the necessary bond strength to support a desired inflation pressure while minimizing a length of the bonded portion in order to reduce the amount of material and overall profile of the delivery system 10. For some embodiments, the proximal neck portion 63 and distal neck portion 63' may have an axial length of at least about 4 mm, more specifically, about 4 mm to about 8 mm.

In some cases, the inflatable balloon 62 may be formed into a pleated configuration while in an uninflated state in order to keep the uninflated profile of the inflatable balloon 62 to a minimum. In some instances, inflatable balloon embodiments 62 may be machine folded (or folded by any other suitable means) to include about 5 pleats to about 10 pleats, more specifically, about 6 pleats to about 8 pleats, as shown in FIG. 6. For some such embodiments, the distal ends of the pleats may be folded over a distal neck portion 63' of the inflatable balloon 62 in order to shift some of the bulk of the inflatable balloon while in an uninflated state away from the structure of the radiopaque markers 32 and/or self-expanding anchor member 24. It may be generally desirable to avoid overlap of the inflatable section 55 of the inflatable balloon 62 with either the radiopaque markers 32 or the self-expanding anchor member 24 in order to keep the outer size profile of the delivery system 10 to a minimum and to minimize a risk of damage to the inflatable section 55 of the inflatable balloon 62 due to contact with the self-expanding anchor member 24.

Regarding the dimensions of the inflatable balloon embodiments 62 discussed herein, both a working length and overall length of the inflatable balloon 62 may be considered. The working length extends along a full diameter length portion of the inflatable balloon 62 where an outer surface of the inflatable balloon 62 is configured to contract and apply outward pressure onto an inside surface of the endoluminal prosthesis 12 when the inflatable balloon is in an inflated state. The overall length includes all of the inflatable section 55 including the tapered conical type sections at one or both ends of the inflatable balloon 62. For purposes of the discussion herein, the working length of the inflatable balloon 62 is indicated by arrow 51 and the overall length of the inflatable balloon 62 is indicated by arrow 53 in FIG. 11.

For some embodiments, the inflatable balloon 62 may include an outer transverse dimension/diameter of about 10 mm to about 26 mm and a working length of about 15 mm to about 50 mm, more specifically, about 15 mm to about 40 mm. Some embodiments may include a working length of about 15 mm to about 25 mm, more specifically, about 18 mm to about 22 mm. In some cases, inflatable balloon embodiments 62 made from a substantially non-compliant material may have an outer diameter of about 26 mm for use with an endoluminal prosthesis 12 having a tubular main graft portion with an inner lumen diameter of about 26 mm. Some inflatable balloon embodiments 62 made from a substantially non-compliant material may have an outer diameter of about 15 mm to about 22 mm and an axial length of about 16 mm to about 20 mm for use with endoluminal prosthesis embodiments 12 having a main graft portion with an inner lumen diameter of about 15 mm to about 22 mm. In some cases, an inflatable balloon 62 made from a compliant material having an outer diameter of about 16 mm to about 19 mm and working length of about 16 mm to about 20 mm may be used with delivery system embodiments 10 having an endoluminal prosthesis 12 with a main graft portion with an inner lumen diameter of about 26 mm. Some inflatable balloon embodiments 62 may have a working length of about 18 mm to about 21 mm, an overall length of about 32 mm to about 38 mm, and an outer diameter of about 15 mm to about 26 mm. Some embodiments of the inflatable balloon 62 may be made from a compliant material with an outer diameter of about 16 mm to about 20 mm, a working length of about 16 mm to about 20 mm and an overall length of about 32 mm to about 38 mm. Such an inflatable balloon embodiment 62 may be used in some cases with an endoluminal prosthesis 12 having an inner lumen diameter of about 15 mm to about 26 mm.

In order to minimize incursion of the inflatable balloon 62 into the main lumen channel 18 proximally beyond the most proximal point of contact between the inflatable balloon 62 and the main graft portion 24 of the endoluminal prosthesis 12, it may be desirable in some cases for the proximal end surface 70 of the balloon 62 to be relatively flat or have a cone angle that is close to 180 degrees. For some embodiments, the inflatable balloon 62 may have a proximal end surface 70 with a cone angle 72 (as shown in FIG. 11) of about 160 degrees to about 180 degrees. Some embodiments may have a cone angle 72 of about 120 degrees to about 160 degrees, more specifically, about 125 degrees to about 135 degrees. Some embodiments may have a cone angle 72 of about 80 degrees, to about 120 degrees, more specifically, about 80 degrees to about 100 degrees, and even more specifically, of about 90 degrees to about 98 degrees.

For some inflatable balloon embodiments 62, a wall material of the inflatable balloon 62 may include a compliant material and for other embodiments the wall material of the inflatable balloon 62 may include a substantially non-compliant material. Some inflatable balloon embodiments 62 may also include a laminate structure with multiple layers of material that may include both compliant and substantially non-compliant materials. In some cases, the wall material of the inflatable balloon 62 may include a material such as polyethylene terephthalate (PET), polyamides such as Nylon®, polyether block amides such as Pebax®, polyethylene (PE), polyurethane (PU) and polyvinylchloride (PVC) or the like or any combination thereof. Any of the inflatable balloon embodiments discussed herein may include a double wall thickness of the balloon material of about 0.001 inches to about 0.003 inches. Some inflatable balloon embodiments 62 may have a double wall thickness of about 0.0005 inches to about 0.002 inches, more specifically, about 0.00075 inches to about 0.0015 inches. A double wall thickness is a measurement derived from measuring a thickness of two thicknesses of the wall of the inflatable balloon 62. In this way, the wall thickness of an inflatable balloon 62 may be measured while keeping the inflatable balloon 62 intact.

The delivery catheter 14 may have an outer sheath 74 with an elongate tubular shape and thin wall which is disposed over the elongate shaft 36 and endoluminal prosthesis 12. The outer sheath 34 may be configured to slide over the relative to the elongate shaft and endoluminal prosthesis so as to removably cover the endoluminal prosthesis 12 while in a constrained state. The delivery catheter 14 may also include a proximal nosecone 76 which may have a bullet-shaped profile and a shoulder portion having an outer surface which may be configured to slidingly accept an inner luminal surface of the retractable outer sheath 74.

The delivery system and method embodiments 10 discussed herein may be particularly useful for endoluminal prosthesis embodiments 12 which include one or more inflatable portions. Such inflatable endoluminal prosthesis embodiments 12 that may be deployed by the systems and methods discussed herein are discussed in U.S. Pat. No. 7,147,660 filed by M. Chobotov et al. on Dec. 20, 2002, titled "Advanced Endovascular Graft" which is hereby incorporated by reference herein in its entirety.

Figure 34:
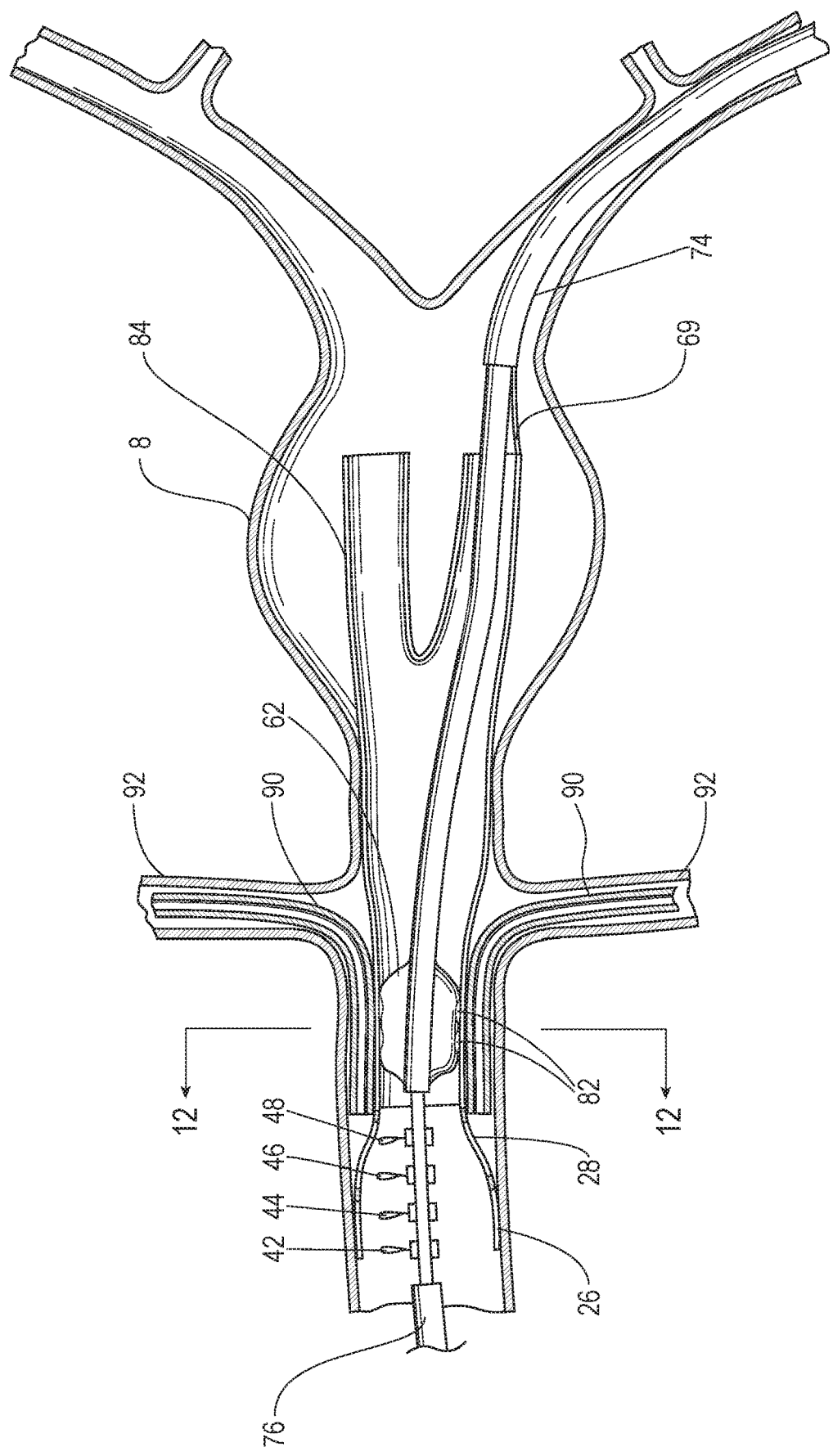
FIG. 34 is an elevation view of an endoluminal prosthesis system embodiment that includes an inflatable balloon and a pair of opposed chimney graft portions being deployed within a patient's vasculature so as to maintain patency of the patient's renal arteries.

For some embodiments, an optional inflatable portion 80 of the graft portion 16 of the endoluminal prosthesis may include one or more inflatable cuffs 82 and/or one or more inflatable channels (not shown) formed from the flexible material of the main graft portion and legs 84 (see the bifurcated legs shown in the embodiment of FIG. 34). For the embodiment shown, the inflatable cuffs 82 are disposed on a proximal portion of the main graft portion 16. A fill tube 69 may also be configured to be coupled to and in fluid communication with a distal end of a fill port 88 (shown in FIG. 9) of the inflatable portion 80 of the endoluminal prosthesis 12. The fill tube 69 may also be uncoupled from the inflation port 88. The fill tube's outer transverse dimension may be configured to slide within an inner lumen of the fill port 88 and provide a seal there between for viscous fluids. For such embodiments, the delivery catheter 14 may include the fill tube 69 including the fill lumen 64 extending axially within the elongate shaft 36 from a proximal section to a distal section of the elongate shaft 36.

In some cases, delivery system embodiments 10 discussed herein may include a delivery catheter 14 with an endoluminal prosthesis 12 such as a stent graft in a radially constrained state releasably disposed on a proximal section 38 of the delivery catheter 14. Such a delivery catheter 14 may include some or all of the features, dimensions or materials of delivery systems discussed in commonly owned U.S. Patent Application Publication No. 2004/0138734, published Jul. 15, 2004, filed Oct. 16, 2003, by Chobotov et al., titled "Delivery System and Method for Bifurcated Graft" and in PCT International Publication No. WO 02/083038, published Oct. 24, 2002, filed Apr. 11, 2001, by Chobotov et al., titled "Delivery System and Method for Bifurcated Graft" each of which is incorporated by reference herein in its entirety.

The endoluminal prosthesis 12, or any other prosthesis discussed herein, may include some or all of the features, dimensions or materials of the prostheses discussed in commonly owned U.S. Patent Publication No. 2009/0099649, filed Oct. 3, 2008, by Chobotov et al., titled Modular Vascular Graft for Low Profile Percutaneous Delivery, which is incorporated by reference herein in its entirety.

For some deployment methods, it may be helpful to radially expand the portion of the endoluminal prosthesis 12 (such as the interface portion between the anchor member portion 24 and the main graft portion 16) which may include radiopaque markers 32 (such as circumferentially disposed radiopaque markers lying in a common plane) in order to accurately visualize the partially deployed stent graft 12 prior to full deployment of the stent graft. In such cases, it may be helpful to have the circumferentially disposed radiopaque markers 32 radially expanded in an outward direction from the position they occupy in a radially constrained state to a position which is in relatively close proximity to an inner surface of a vessel 9 in which the endoluminal prosthesis 12 is being deployed. Such a deployment protocol may be particularly useful for endoluminal prosthesis embodiments 12 such as stent grafts that do not include a connector ring structure in a proximal end of the graft portion 16 of the stent graft 12. This is because a self-expanding type connector ring may be useful in some cases to assist with outward radial expansion of the proximal end or flap of the graft portion of the stent graft after the distal portion of the proximal self-expanding anchor member 24 has been released. For some endoluminal prosthesis embodiments 12 that do not have self-expanding connector rings, the proximal end or flap 20 of the graft portion 16 of the stent graft may only open about 10 mm or so which may not be conducive to accurate imaging and positioning using observation of parallax of the radiopaque markers 32 during deployment.

Regarding the use of the delivery system embodiments 10 and 110 discussed herein, deploying an endoluminal prosthesis 12 may include advancing a delivery system 10 into a patient's vasculature which includes an elongate shaft 36 and an endoluminal prosthesis 12 releasably secured to the elongate shaft 36. The method may also include releasing an outer constraint from a graft portion 16 of the endoluminal prosthesis 12 such as by retracting the outer sheath 74 of the delivery catheter 14. An outer radial constraint may then be partially released from the self-expanding anchor member 24 of the endoluminal prosthesis 12 (as shown in FIG. 9) by releasing the first distal releasable belt 46 and second distal releasable belt 48 to allow the self-expanding anchor member 24 to partially deploy. Thereafter, the inflatable balloon 62 may be inflated and radially expanded so as to radially expand a portion of a graft portion 16 of the endoluminal prosthesis 12 which is disposed adjacent the inflatable balloon 62. In some cases, the inflatable balloon 62 may be is disposed within a main inner lumen 18 of the graft portion 16 of the endoluminal prosthesis 12 with a proximal end of the inflatable balloon 62 being disposed adjacent but distal of the self-expanding anchor member 24. In some cases, the inflatable balloon 62 may be is disposed within a main inner lumen 18 of the graft portion 16 of the endoluminal prosthesis 12 with a proximal end of the inflatable balloon 62 being disposed adjacent but distal of a plurality of radiopaque markers 32 which may be circumferentially disposed adjacent a proximal edge 20 of the graft portion of the endoluminal prosthesis 12. An outer radial constraint on the self-expanding anchor member 24 may then be fully released so as to fully deploying the self-expanding anchor member 24 of the endoluminal prosthesis 12.

In some cases, inflating and radially expanding the inflatable balloon 62 may include inflating and radially expanding the inflatable balloon 62 so as to apply an outward radial force onto an inner surface of a main inner lumen 18 of a graft portion 16 of the endoluminal prosthesis 12 until an outer surface of the graft portion 16 adjacent the inflatable balloon 62 is urged into contact with an inner surface of the patient's vasculature 8. The saline or other inflation fluid may then be injected through the inflation lumen 60 of the elongate shaft 36 and enter an interior volume of the inflatable balloon 62 at the desired pressure. In some cases, inflating the inflatable balloon 62 includes inflating the interior volume of the inflatable balloon 62 with a sterile incompressible fluid such as saline at a pressure of about 3 psi to about 9 psi and in some cases to a pressure of up to about 1 atmosphere within the inflation lumen 60. The pressurized saline may be injected with a device such as an Endoflator® or standard syringe by coupling the inflation device to a connector such as a Luer type connector on the distal adapter 54. In some instances, the interior volume of the inflatable balloon 62 may be inflated with a mixture of saline and contrast media in order to improve the ability to image the inflated or partially inflated inflatable balloon 62 using fluoroscopy or the like. For some embodiments, a mixture of about 25% contrast media and about 75% saline may be used, in other embodiments, a mixture of about 20% contrast media and about 80% saline may be used. With regard to inflation of some inflatable balloon embodiments 62, the interior volume of the inflatable balloon 62 may be about 6 ml to about 20 ml.

In some cases, the endoluminal prosthesis 12 may be axially repositioned within the patient's vessel 9 after partially deploying the self-expanding anchor member 24 and before fully deploying the self-expanding anchor member 24. In such cases, it may be desirable to deflate the inflatable balloon 62 prior to repositioning the endoluminal prosthesis 12. For endoluminal prosthesis embodiments 12 that include an inflatable portion 80, it may also be desirable to inflate the inflatable portion 80 of the endoluminal prosthesis 12 after inflation of the inflatable balloon 62 in order to promote sealing and conformance of the inflatable cuffs 82 (if any) to an inner surface of a patient's vessel 9. In such cases, it may also be desirable for the working length (as indicated by arrows 51) of the inflatable balloon 62 to be positioned axially coextensively with the inflatable cuffs 82. For such embodiments, the outward radial force imposed by the outer surface of the inflatable balloon 62 upon inflation may be useful in order to assist with sealing and apposition of one or more inflatable cuffs 82 against an inner luminal surface of the patient's vasculature 9. In some cases, the inflatable balloon 62 may be used to expand one or more inflatable cuff embodiments 82 in an outward radial direction without similarly expanding the self-expanding anchor member 24. For some such embodiments, it may be desirable to have an inflatable balloon 62 as discussed herein that is disposed within the endoluminal prosthesis 12 such that the inflatable balloon 62 is disposed so as to be axially coextensive and axially overlapping a first inflatable cuff 82 but not be axially coextensive or axially overlap a second inflatable cuff 82 of the same endoluminal prosthesis 12.

For some deployment method embodiments, it may be desirable to align the endoluminal prosthesis 12 prior to deployment such that an imaginary plane which intersects the circumferentially disposed radiopaque markers 32 is orthogonal to a longitudinal axis of the target vessel 9 at the position of the circumferentially disposed radiopaque markers 32. Examples of deployment devices, alignment devices, radiopaque markers 32, delivery methods and the like that may be used in conjunction with any suitable system or component thereof discussed herein may be found in commonly owned U.S. Patent Application No. 2011/0218609, filed Feb. 9, 2011, by M. Chobotov et al., and titled "Fill Tube Manifold and Delivery Methods for Endovascular Graft", and U.S. Patent Publication No. 2013/0268048, filed Mar. 15, 2013, by J. Watson et al., and titled "Delivery Catheter for Endovascular Device", U.S. Patent Publication No. 2013/0268044, filed Mar. 13, 2013, by D. Parsons et al., and titled "Durable Stent Graft with Tapered Struts and Stable Delivery Methods and Devices", each of which is hereby incorporated by reference herein in its entirety.

For any of the delivery system embodiments 10 discussed above, embodiments of the inflatable balloon 62 may have an axial length of about 25 to about 27 mm and a transverse diameter of about 16 mm to about 18 mm when in an inflated state. Such an inflatable balloon 62 may be inflated through an inflation lumen 60 having an inner transverse lumen diameter of about 0.014 inches to about 0.016 inches.

For any of the embodiments of the delivery systems 10 discussed above, the inflatable balloon 62 may be made from a compliant material such as urethane with an outer diameter of about 25 mm to about 26 mm and an axial length of about 25 mm. An inflatable balloon 62 so sized may be useful for delivery of an endoluminal prosthesis 12 having an inner lumen diameter of 26 mm (including an Ovation® type stent graft device manufactured by Tri Vascular, Inc., Santa Rosa, Calif.). The inflatable balloon 62 may be bonded or otherwise secured to the elongate shaft 36 close to a proximal end or proximal flap 20 of the main graft section 16 of the endoluminal prosthesis 12 with an ultraviolet cured adhesive. An axial length of about 25 mm for the inflatable balloon 62 may be sufficient in some embodiments to allow the inflatable balloon 62 to axially overlap the inflatable cuffs 82 disposed at a distal section of the graft section 16 of the endoluminal prosthesis 12. For such embodiments, it may be desirable that the inflatable balloon 62 not axially overlap the radiopaque markers 32 adjacent the proximal end 20 of the main graft portion 16. The proximal end face 70 of the balloon embodiment may be flat (that is, with a cone angle 72 of about 180 degrees) or even overhanging.

The inflation lumen 60 for the inflatable balloon 62 may be made from a thin walled material such as polyimide with an inner lumen diameter of about 0.01 inches to about 0.02 inches to enable filling of the inflatable balloon 62 in a few seconds, such as about 15 seconds, using high flow fluids such as saline or the like. In some embodiments, the inflation lumen 60 may have an inner lumen diameter of about 0.020 inches to about 0.025 inches to enable quicker filling and inflation of the inflatable balloon 62. The inflation of such an inflatable balloon embodiment 62 may be carried out with a syringe (not shown) connected to a Luer type fitting on the distal adapter 54.

In use, after the release wire 52 securing the first distal releasable belt 46 and second distal releasable belt 48 is retracted to deploy these releasable belts, the inflatable balloon 62 may be inflated by hand with a syringe or the like. In some cases, the inflatable balloon 62 may be initially inflated to an outside dimension or diameter of about 8 mm prior to release of this release wire 52. In some cases, the inflatable balloon 62 may be inflated until the proximal end or proximal flap 20 of the graft portion 16 of the endoluminal prosthesis 12 and radiopaque markers 32 disposed adjacent thereto are radially expanded in an outward direction almost to an inner surface of the wall of the vessel 9 being treated. In some instances, the inflatable balloon 62 may be inflated to an outer transverse dimension or diameter of about 15 mm after release of this release wire 52. After accurately positioning the endoluminal prosthesis 12 in an axial direction with respect to the patient's renal arteries 92 (or any other suitable reference point) the other release wire 50 may be retracted and the proximal self-expanding anchor member fully deployed.

The inflatable balloon 62 may then be deflated prior to inflating an optional inflatable portion 80 of the endoluminal prosthesis 12. In some instances, the inflatable portion 80 of the endoluminal prosthesis 12 may be inflated while the inflatable balloon 62 is still inflated. For such cases, it may be desirable for the inflatable balloon 62 to be maintained at an internal inflation pressure which is less than an inflation pressure of the fill material being injected into the optional inflatable portion 80 of the endoluminal prosthesis 12. After inflation of the inflatable portion 80 of the endoluminal prosthesis 12, the fill tube 69 may be demated and the elongate shaft 36 of the delivery catheter 14 withdrawn in a distal direction from within the endoluminal prosthesis 12. Using the inflatable balloon 62 to apply outward radial force on the graft portion 16 of the endoluminal prosthesis 12 during deployment may also be useful in eliminating type I endoleaks if present during the deployment process. This may be particularly true for embodiments that include optional inflatable cuffs 82 on the graft portion 16 of the endoluminal prosthesis 12.

In some cases, the inflatable portion 80 of the endoluminal prosthesis 12 remains coupled to the fill tube 69 for a predetermined amount of time after initiation of fill of the inflatable portion 80 with a fill material such as a polymerizable or curable fill material. After the predetermined time has elapsed, the inflatable balloon 62 may then be positioned across both optional inflatable cuffs 82 and inflated to a suitable inflation pressure such as about 3 psi to about 6 psi. In some cases, the predetermined amount of elapsed time prior to inflating the inflatable balloon to expand the filled cuffs 82 in an outward radial direction may be about 14 minutes, in some instances, exactly 14 minutes. Such a procedure may be useful to resolve endoleaks. Once resolved, or other appropriate end point is achieved, the inflatable balloon 62 may be deflated and the fill tube 69 demated from the fill port of the inflatable portion 80 of the endoluminal prosthesis 12.

For some embodiments, an endoluminal prosthesis 12 in the form of a stent graft having a graft portion 16 with an inner diameter of about 29 mm when in an expanded state and proximal self-expanding anchor member 24 having an outer diameter of about 34 mm when in an expanded state may be loaded into a delivery catheter having an outer sheath with an outer diameter of about 15 French. This combination resulted in an outer sheath retraction force of about 18 pounds for unsheathing movement of the outer sheath 74. In this particular example, the radial expansion achieved after release of the distal portion of the proximal self-expanding anchor member 24 and initial inflation of the balloon was from about 10 mm to about 17 mm×about 11 mm. The inflatable balloon 62 also had a tapered configuration that ultimately achieved an inflated dimension of about 20 mm outer diameter and an axial length of about 7 mm. This inflatable balloon took about 1 minute to fill through an inflation lumen 60 having an inner diameter of about 0.015 inches. The delivery catheter 14 did not include a crossover lumen.

For some embodiments, an endoluminal prosthesis 12 in the form of a stent graft having a graft portion 16 with an inner diameter of about 26 mm when in an expanded state and proximal self-expanding anchor member 24 having an outer diameter of about 34 mm when in an expanded state may be loaded into a delivery catheter 14 having an outer sheath 74 with an outer diameter of about 15 French. This combination resulted in an outer sheath retraction force of about 7 pounds for unsheathing movement of the outer sheath 74. In this particular example, the radial expansion achieved after release of the distal portion 28 of the proximal self-expanding anchor member 24 and initial inflation of the balloon 62 was from about 10 mm to about 25 mm. The inflatable balloon 62 also had a tapered configuration that ultimately achieved an inflated dimension of about 20 mm outer diameter and an axial length of about 7 mm. This inflatable balloon took about 16 seconds to fill about 5 ml of saline through an inflation lumen 60 having an inner diameter of about 0.02 inches by hand injection. The delivery catheter 14 did not include a crossover lumen.

For some embodiments, an endoluminal prosthesis 12 in the form of a stent graft having a graft portion 16 with an inner diameter of about 26 mm when in an expanded state and proximal self-expanding anchor member 24 having an outer diameter of about 34 mm when in an expanded state may be loaded into a delivery catheter 14 having an outer sheath 74 with an outer diameter of about 15 French. This combination resulted in an outer sheath retraction force of about 9 pounds for unsheathing movement of the outer sheath 74. In this particular example, the radial expansion achieved after release of the distal portion of the proximal self-expanding anchor member 24 and initial inflation of the balloon 62 was from about 10 mm to about 19 mm and ultimately to about 25 mm at maximum inflation. The inflatable balloon 62 also had a tapered configuration that ultimately achieved an inflated dimension of about 20 mm outer diameter and an axial length of about 7 mm. This inflatable balloon took about 15 seconds to fill about 6 ml of saline through an inflation lumen having an inner diameter of about 0.025 inches by hand injection. The delivery catheter 14 did include a crossover lumen, a fill port at the distal adapter 54 and retraction of the balloon 62 during the procedure was acceptable.

For some embodiments, an endoluminal prosthesis 12 in the form of a stent graft having a graft portion 16 with an inner diameter of about 26 mm when in an expanded state and proximal self-expanding anchor member 24 having an outer diameter of about 34 mm when in an expanded state may be loaded into a delivery catheter 14 having an outer sheath 74 with an outer diameter of about 14 French. This combination resulted in an outer sheath retraction force of about 13 pounds for unsheathing movement of the outer sheath 74. In this particular example, the radial expansion achieved after release of the distal portion of the proximal self-expanding anchor member 24 and initial inflation of the balloon 62 was from about 10 mm to about 20 mm. The inflatable balloon 62 also had a standard configuration that ultimately achieved an inflated diameter of about 15 mm and an axial length of about 25 mm. This inflatable balloon was filled through an inflation lumen having an inner diameter of about 0.025 inches. The delivery catheter 14 did include a crossover lumen 71 and a fill port at the distal adapter 54. This particular example was used in conjunction with a chimney type graft 90 (6 mm Viabahn® graft manufactured by Gore Enterprises, Flagstaff, Ariz.) and a compliant Coda® balloon model 32 mm, manufactured by Cook Medical located in Bloomington Ind., during the fill and no gutter type channels were observed with the Coda balloon inflated or when deflated.

For some embodiments, an endoluminal prosthesis 12 in the form of a stent graft having a graft portion 16 with an inner diameter of about 22 mm when in an expanded state and proximal self-expanding anchor member 24 having an outer diameter of about 29 mm when in an expanded state may be loaded into a delivery catheter 14 having an outer sheath 74 with an outer diameter of about 14 French. This combination resulted in an outer sheath retraction force of about 15 pounds for unsheathing movement of the outer sheath 74. In this particular example, the radial expansion achieved after release of the distal portion of the proximal self-expanding anchor member 24 and initial inflation of the balloon 62 was from about 8 mm to about 21 mm. The inflatable balloon ultimately achieved an inflated diameter of about 10 mm and an axial length of about 15 mm. This inflatable balloon 62 was filled through an inflation lumen 60 having an inner diameter of about 0.025 inches to an inflation pressure of about 6 psi with water. The delivery catheter 14 did include a crossover lumen 71 and a fill port at the distal adapter 54. This particular example was used in conjunction with a chimney type graft 90 (5 mm tygon type tubing) and a non-compliant balloon 62 and during the fill a good seal was made after demate of the fill tube 69.

Some endoluminal prosthesis embodiments 12 may include a graft portion 16 with an inner diameter of about 26 mm when in an expanded state and proximal self-expanding anchor member 24 having an outer diameter of about 34 mm when in an expanded state. Such an endoluminal prosthesis 12 may be loaded into a delivery catheter 14 having an outer sheath 74 with an outer diameter of about 15 French. The inflatable balloon 62 for this embodiment may be made from polyurethane with a durometer of about 90 A and a double wall thickness of 0.001 inches. The inflatable balloon may include an outer diameter of about 18.5 mm, a working length of about 20 mm and an overall length of about 38 mm. The inflatable balloon cone angle may be about 46 to about 48 degrees on each side for a full cone angle 72 of about 92 degrees to about 96 degrees. The elongate shaft 36 may be made from a polyurethane material with a durometer of about Shore 72D. The elongate shaft 36 may further have an outer diameter of about 0.105 inches and extend an entire axial length of the endoluminal prosthesis 12. Such an embodiment may yield a retraction force for the outer sheath 74 of about 11 pounds for unsheathing movement of the outer sheath 74. In this particular example, the radial expansion achieved after release of the distal portion of the proximal self-expanding anchor member 24 and initial inflation of the balloon 62 may be from about 8 mm to about 20 mm with an interior volume of the inflatable balloon 62 partially inflated to about 10 ml. Such an inflatable balloon embodiment 62 may ultimately achieve an inflated diameter of about 26 mm, which may be consistent with the inner lumen size of the associated endoluminal prosthesis, when filled to its maximum inflation volume of about 19 ml. This inflatable balloon 62 may be filled through an oval inflation lumen 60 having a minor inner transverse of about 0.025 inches and a major inner transverse dimension of about 0.055 inches. Inflation of such an inflatable balloon embodiment 62 may take about 18 seconds to fill about 19 ml of 4 to 1 saline to contrast mixture through the inflation lumen by hand injection. The corresponding delivery catheter 14 may include a crossover lumen 71 and a fill port at the distal adapter 54.

Figure 14:
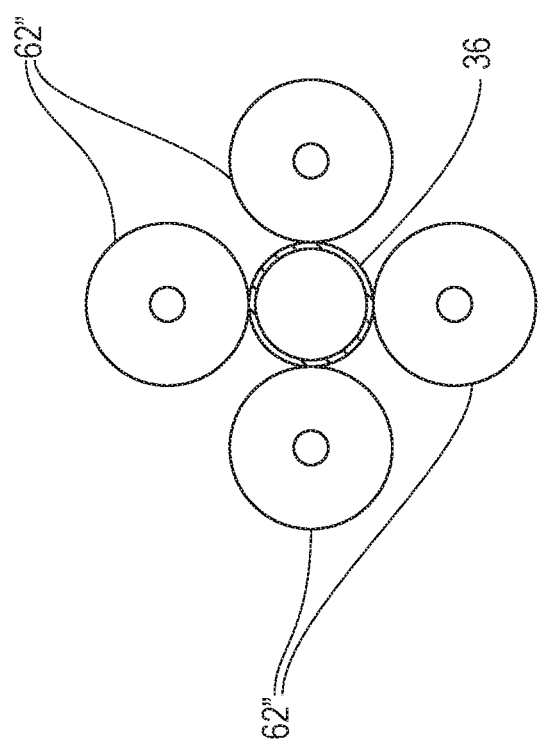
FIG. 14 is a schematic view in transverse section of a perfusion inflatable balloon embodiment.
Figure 13:
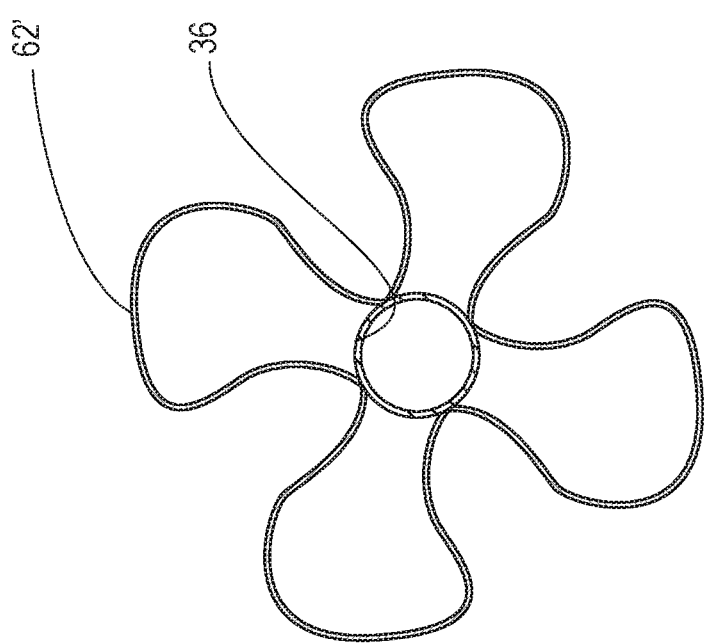
FIG. 13 is a schematic view in transverse section of a perfusion inflatable balloon embodiment.
Figure 15:
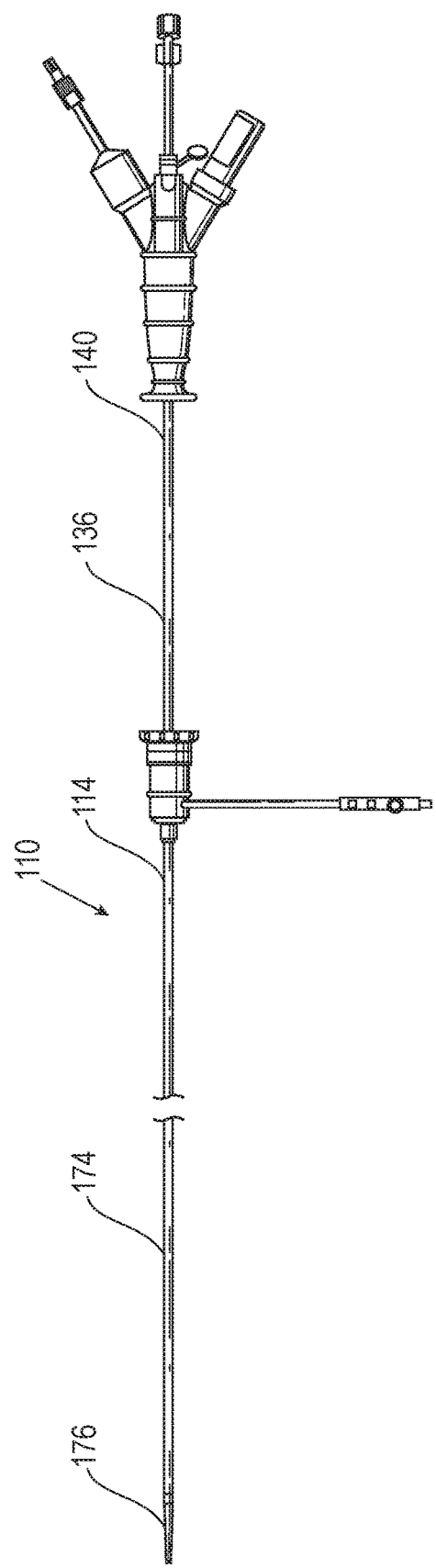
FIG. 15 is an elevation view of a delivery system embodiment.
Figure 16:
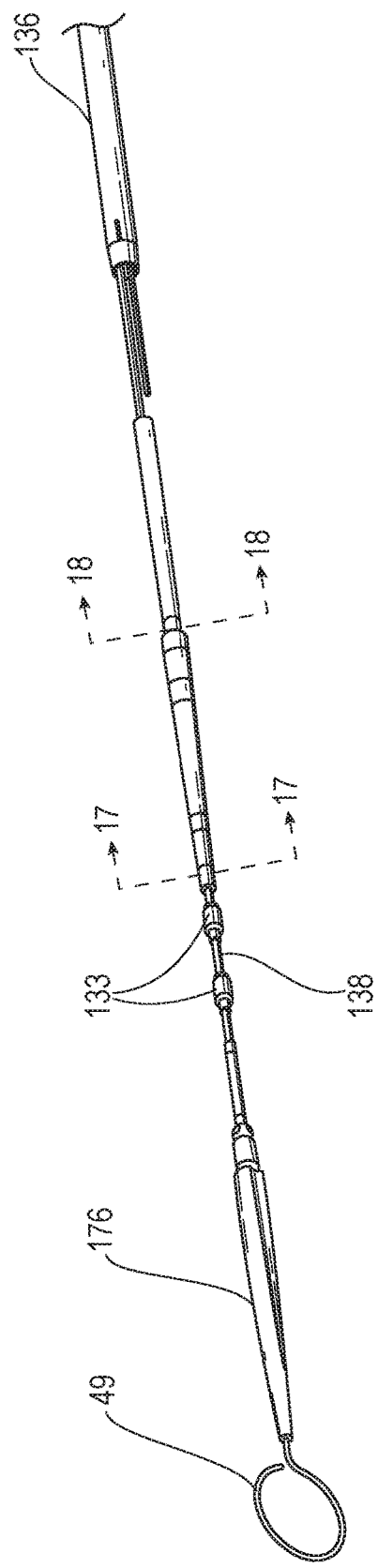
FIG. 16 is a perspective view of a portion of the delivery system embodiment of FIG. 15 with an outer sheath not shown.
Figure 18:
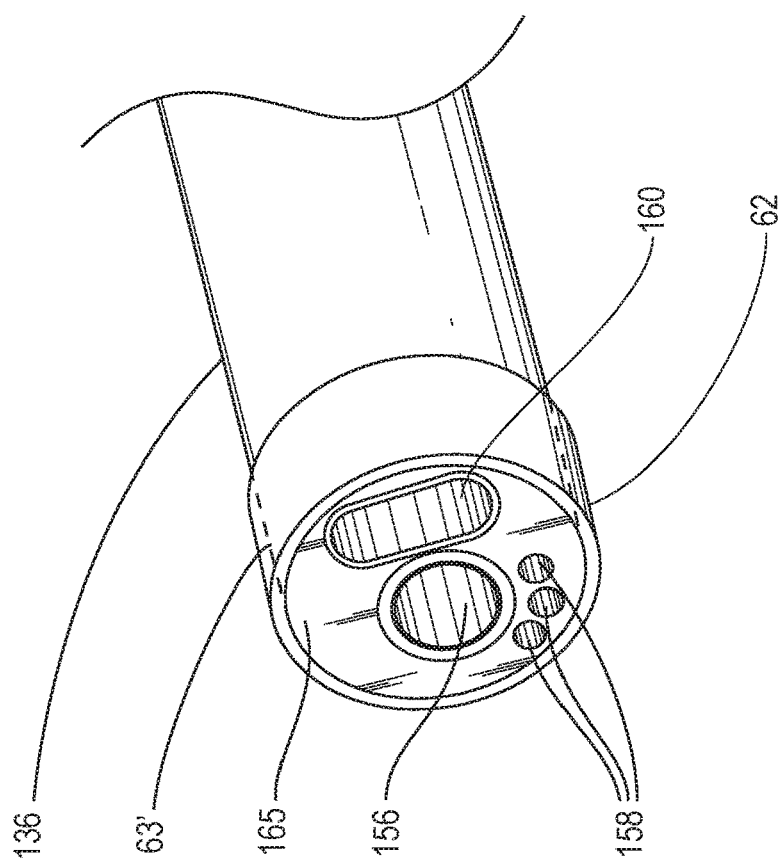
FIG. 18 is a transverse cross section of the delivery system embodiment of FIG. 16 taken along lines 18-18 of FIG. 16.
Figure 17:
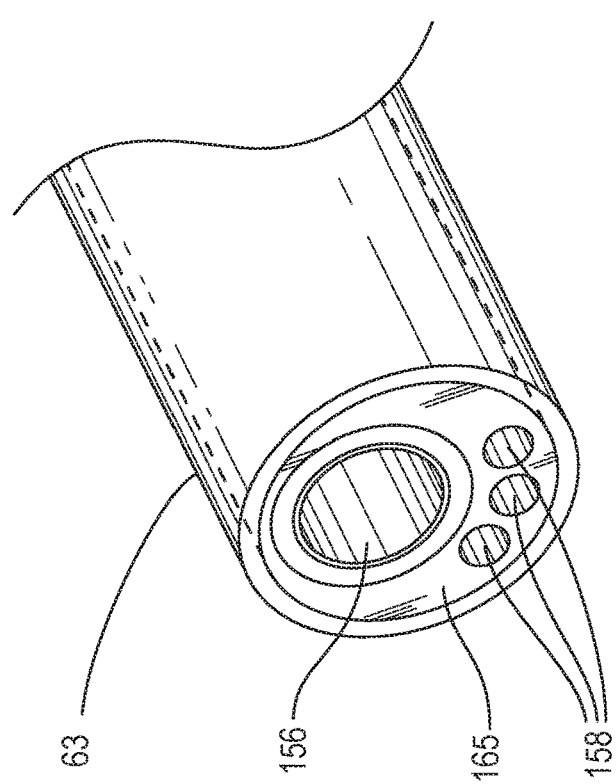
FIG. 17 is a transverse cross section of the delivery system embodiment of FIG. 16 taken along lines 17-17 of FIG. 16.
Figure 19:
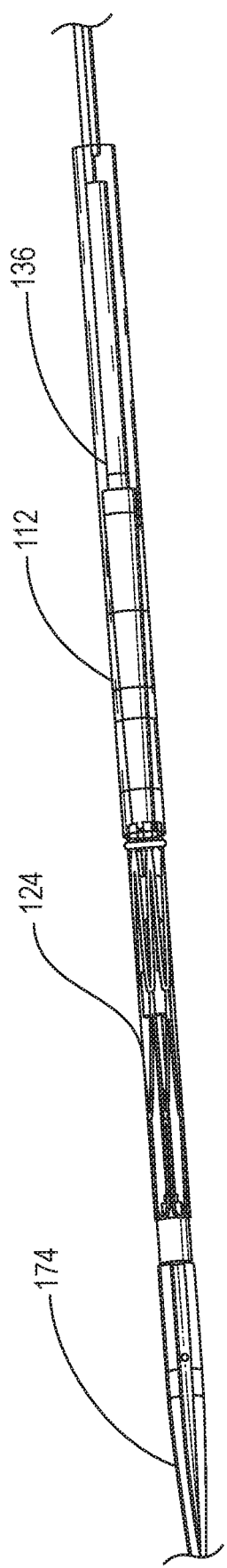
FIG. 19 is a perspective view of a portion of the delivery system embodiment of FIG. 15.
Figure 20:
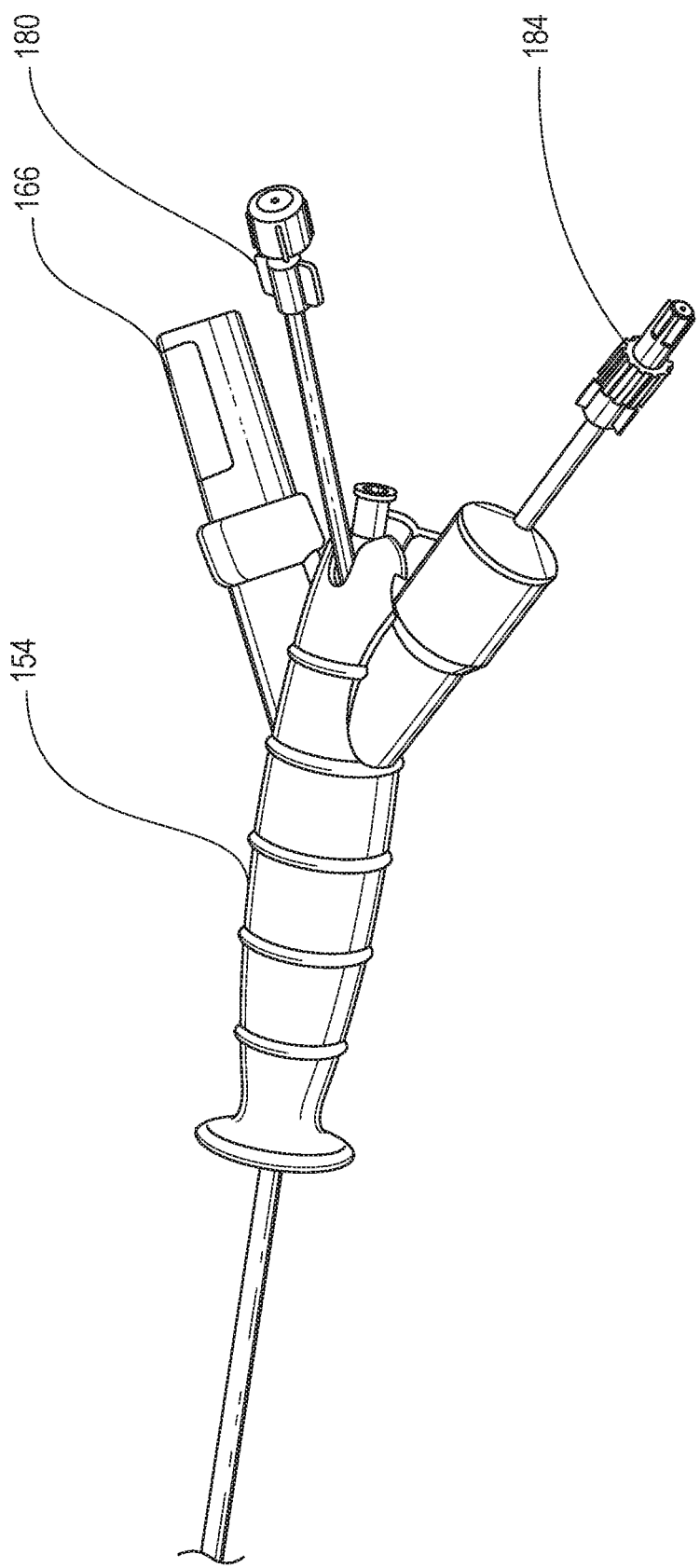
FIG. 20 is a perspective view of an embodiment of a distal adapter.
Figure 21:
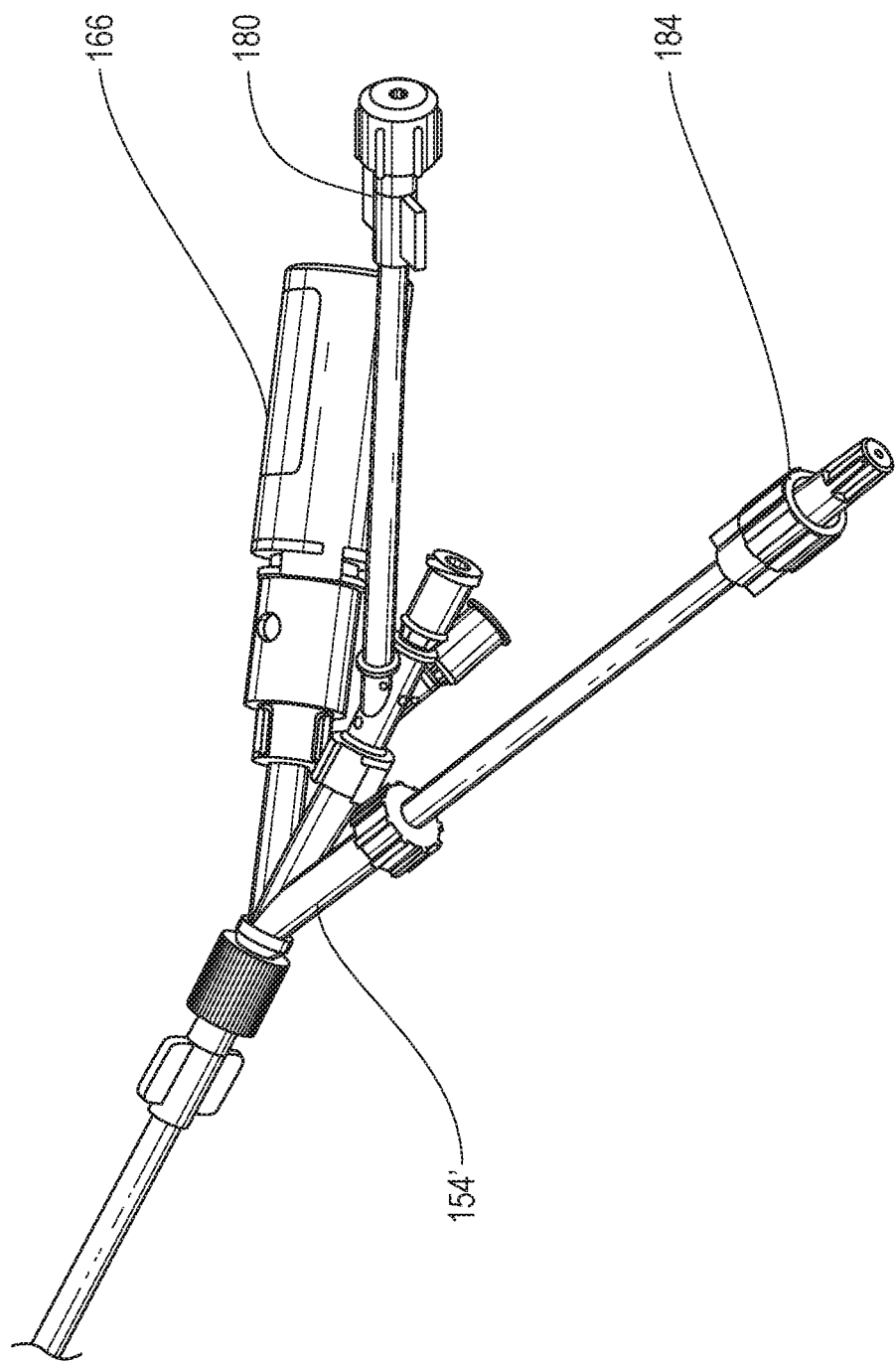
FIG. 21 is a perspective view of an embodiment of a distal adapter.
Figure 22:
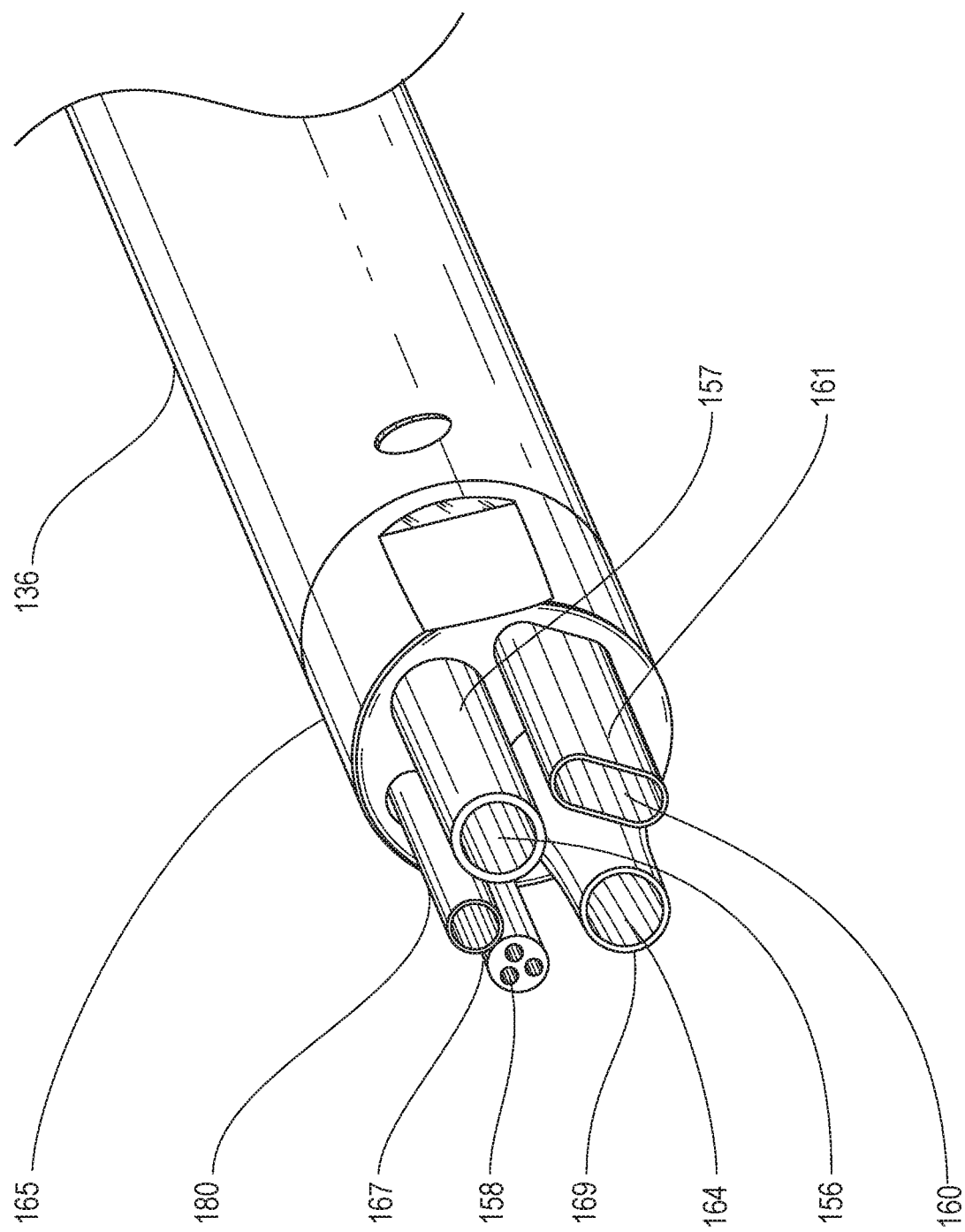
FIG. 22 is a perspective view in partial section of a portion of an elongate shaft embodiment of the delivery system of FIG. 15.

For any of the inflatable balloon embodiments discussed herein, it may be desirable to include means (shown in FIGS. 13 and 14) for allowing blood perfusion past the inflatable balloon 62 while the inflatable balloon 62 is in an inflated state. This may be applicable for indications that include treatment of thoracic aortic aneurysms and abdominal aortic aneurysms. This may be particularly true for the larger thoracic aorta where such perfusion means including perfusion holes, a flower petal shape inflatable balloon 62' as shown in FIG. 13 or multiple small inflatable balloons 62" as shown in FIG. 14 bunched together may be useful to avoid migration of the endoluminal prosthesis during deployment as well as allowing blood flow during inflation. For some embodiments, the number of flower petal shape inflatable balloons 62' or multiple small inflatable balloons 62" disposed about the shaft 36 may be about 3 to about 5 balloons 62".

FIGS. 15-26 illustrate embodiments of delivery systems for treatment of a vascular defect such as aneurysm 8. The delivery system embodiment 110 may include the endoluminal prosthesis 12 for treatment of the vascular defect 8 and a delivery catheter 114. Generally, the delivery system 110 may include the same or similar materials, dimensions and features as those of the delivery system 10 discussed above. Where appropriate, like reference numerals will be used for like elements with respect to the delivery system 10 discussed above and delivery system 110. As shown, delivery system 110 includes a multi-lumen member 165 that may include an elongate multi-lumen member 165 for use within the elongate shaft 136 to facilitate the various functions of the delivery catheter and the elements thereof.

As discussed above, the endoluminal prosthesis 12 may include a tubular main graft portion 16 made from a thin flexible material, and including a main inner lumen 18, a proximal end 20 and a distal end 22. The graft body may be formed from a flexible and supple graft material, such as PTFE, and have a main fluid flow lumen disposed in a main graft portion therein.

For some embodiments, the delivery catheter 114 of the delivery system 110 may include an elongate shaft 136 with sufficient column strength for percutaneous advancement within a patient's vasculature 8, the elongate shaft 136 also having a proximal section 138 and a distal section 140. A plurality of releasable belts may be disposed on the proximal section 138 of the elongate shaft 136 and configured to releasably constrain a self-expanding anchor member of an endoluminal prosthesis. A plurality of appropriately sized cylindrical bushings or pads 133 may be secured over the elongate shaft adjacent one or more of the releasable belts in order to properly space the self-expanding anchor member 124 or portions thereof while in a constrained state. A plurality of elongate release members may be disposed in operative communication with a distal section of the elongate shaft 136 and said elongate release members may each include a proximal section configured to releasably secure at least one respective releasable belt while said releasable belt is in a configuration that constrains at least a portion of the self-expanding anchor member 124 of the endoluminal prosthesis 112.

The elongate shaft 136 of such a delivery catheter embodiment 114 may include one or more release member lumens 158 extending within a release member sleeve 167, a guidewire lumen 156 extending within a guidewire tube 157, an inflation lumen 160 for inflation of an inflatable balloon 162 extending within an inflation tube 161 and an optional fill lumen 164 for filling an optional inflatable portion of the endoluminal prosthesis 112 extending within a fill tube 169. The section of the elongate shaft 136 of the delivery catheter embodiment 114 illustrates the release member lumens 158 and guidewire lumen 156, surrounded by guidewire tube 157.

Each of these lumen embodiments 156, 158, 160 and 164 and tube or sleeve embodiments 157, 161, 167 and 169 may extend axially along or within the elongate shaft 136 of the delivery catheter 114 from a proximal section to a distal end thereof, including to the distal adapter 154 at the distal end of the elongate shaft 136. In some cases, the release members (not shown) may be coupled to respective deployment knobs 166 disposed on the distal adapter 154.

The inflatable balloon 62 which may be integrally formed with the elongate shaft 136 may be operatively secured to the elongate shaft 136 of the delivery catheter 114 within the main inner lumen 118 of the tubular main graft portion 116 of the endoluminal prosthesis 112. In some instances, the inflatable balloon 62 may be disposed in an axial position wherein a proximal end 68 of an inflatable section 55 of the inflatable balloon 62 is positioned adjacent but distal of the radiopaque markers 132 with an optional axial gap of up to about 5 mm, in some cases, up to about 2 mm therebetween indicated by arrows 55' shown in FIG. 23 and as discussed in more detail above with regard to the configuration shown in FIGS. 3 and 10. In some cases, the inflatable balloon 62 may be disposed within the non-deployed constrained endoluminal prosthesis 112 in an axial position with the proximal end 68 of the inflatable section 55 of the inflatable balloon 62 disposed distal of the self-expanding anchor member structure such as a self-expanding anchor member 124. The inflatable section 55 of the inflatable balloon 62 may also be disposed with a proximal end 68 of the inflatable section 55 thereof disposed adjacent but distally of any other high strength resilient structures that may be associated with securing an anchor member portion of an endoluminal prosthesis 112 to a main graft portion 116 of an endoluminal prosthesis 112, such as a connector ring. As discussed above, in some cases, there may be an optional axial gap between the proximal end 68 of the inflatable section 55 and distal of the self-expanding anchor member 124 of up to about 5 mm, more specifically, up to about 2 mm.

For some embodiments, the inflatable balloon 62 may have a proximal end surface 70 with a cone angle 72 (as shown in FIG. 11) of about 80 degrees, to about 120 degrees, more specifically, about 80 degrees to about 100 degrees, and even more specifically, of about 90 degrees to about 98 degrees. The full diameter length of the inflatable balloon (indicated by arrows 51 in FIG. 11) may be indicated for imaging under fluoroscopic imaging or the like with a pair of radiopaque markers 135 which are disposed axially coextensive with each respective proximal end and distal end of the full diameter section as shown in FIG. 23. These markers 1 may be useful in some circumstances in order to axially align the inflatable balloon 62 with structures of the endoluminal prosthesis 112, such as the inflatable cuffs 182 of the endoluminal prosthesis 112 discussed below.

The delivery catheter 114 may have an outer sheath 174 with an elongate tubular shape and thin wall which is disposed over the elongate shaft 136 and endoluminal prosthesis 112. The outer sheath 174 may be configured to slide over the relative to the elongate shaft and endoluminal prosthesis so as to removably cover the endoluminal prosthesis 112 while in a constrained state. The delivery catheter 114 may also include a proximal nosecone 176 which may have a bullet-shaped profile and a shoulder portion having an outer surface which may be configured to slidingly accept an inner luminal surface of the retractable outer sheath 174.

For some embodiments, an optional inflatable portion 180 of the graft portion 116 of the endoluminal prosthesis may include one or more inflatable cuffs 182 and/or one or more inflatable channels (not shown) formed from the flexible material of the main graft portion and legs 84 (see the bifurcated legs shown in the embodiment of FIG. 34). A fill tube 169 may also be configured to be coupled to and in fluid communication with a distal end of a fill port 88 (shown in FIG. 9) of the inflatable portion 80 of the endoluminal prosthesis 12. The fill tube 169 may also be uncoupled from the inflation port 88. The fill tube's outer transverse dimension may be configured to slide within an inner lumen of the fill port 88 and provide a seal there between for viscous fluids. For such embodiments, the delivery catheter 114 may include the fill tube 169 including the fill lumen 164 extending axially within the elongate shaft 136 from a proximal section to a distal section of the elongate shaft 136.

In some cases, inflating and radially expanding the inflatable balloon 62 may include inflating and radially expanding the inflatable balloon 62 so as to apply an outward radial force onto an inner surface of a main inner lumen 118 of a graft portion 116 of the endoluminal prosthesis 112 until an outer surface of the graft portion 116 adjacent the inflatable balloon 62 is urged into contact with an inner surface of the patient's vasculature 8. The saline or other inflation fluid may then be injected through the inflation lumen 160 of the elongate shaft 136 and enter an interior volume of the inflatable balloon 62 at the desired pressure. In some cases, inflating the inflatable balloon 62 includes inflating the interior volume of the inflatable balloon 62 with a sterile incompressible fluid such as saline at a pressure of about 3 psi to about 9 psi and in some cases to a pressure of up to about 1 atmosphere within the inflation lumen 60. The pressurized saline may be injected with a device such as an Endoflator® or standard syringe by coupling the inflation device to a connector such as a Luer type connector on the distal adapter 154. In some instances, the interior volume of the inflatable balloon 62 may be inflated with a mixture of saline and contrast media in order to improve the ability to image the inflated or partially inflated inflatable balloon 62 using fluoroscopy or the like.

The inflation lumen 160 for the inflatable balloon 62 may be made from a thin walled material such as polyimide with an inner lumen having an oval shaped transverse section. As discussed above, some oval inflation lumen embodiments 160 may have a major inner transverse dimension of about 0.055 inches to about 0.060 inches, and a minor inner transverse dimension of about 0.024 inches to about 0.028 inches. The inflation of such an inflatable balloon embodiment 62 may be carried out with a syringe (not shown) connected to a Luer type inflation port fitting 180 on the distal adapter 154. The delivery catheter 114 may further include a crossover lumen 182, and a fill port 184 in communication with the fill tube 169 at the distal adapter 154.

FIGS. 27-29 and 31-33 illustrate several multi-lumen member embodiments 65, 65' and 65" that include various embodiments of guidewire tube lumen embodiments 57A, 57A' and 57A", that accommodate guidewire tube 57. Release wire sleeve lumen embodiments 67A, 67A' and 67A" may accommodate release wire sleeve 67. The multi-lumen member embodiments 65, 65' and 65" may be configured as elongate multi-lumen member embodiments in some cases. The release wire sleeve embodiments 67A, 67A' and 67A" may also be configured to accommodate the crossover member 71 in some cases. In addition, the fill tube lumen embodiments 69A, 69A' and 69A" of the respective multi-lumen member embodiments 65, 65' and 65" may be used to contain or surround the fill tube 69. The multi-lumen member embodiments that include the aforementioned elements would typically be disposed distally of the endoluminal prosthesis 12 on the delivery system 14 as the fill tube 69 typically couples to a port at a distal end of the endoluminal prosthesis 12.

Figure 35:
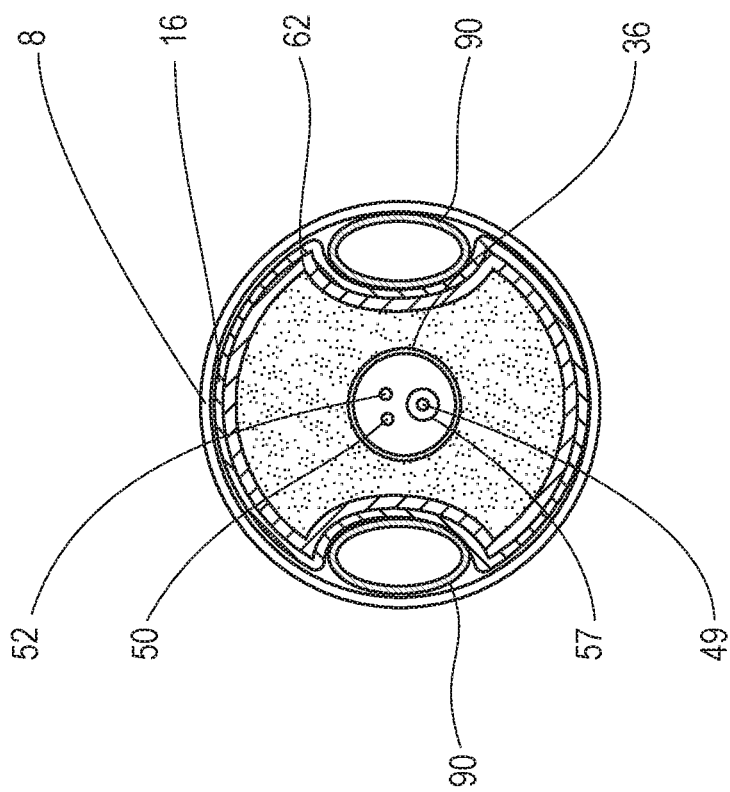
FIG. 35 is a transverse cross section view of the endoluminal prosthesis system embodiment of FIG. 34 taken along lines 35-35 of FIG. 34.

In some method embodiments, it may be desirable to deploy "chimney" type endoluminal prostheses 90 in fluid communication between a patient's renal arteries 92 (or any other suitable side branch arteries of the aorta and downstream vessels of the aorta such as the SMA or celiac arteries) and the aorta prior to deployment of an aortic endoluminal prosthesis 12 as shown in FIGS. 34 and 35. In such methods, particularly where an inflatable endoluminal prosthesis is being used in the aorta, the inflatable balloon 62 may provide enhanced sealing between outer surfaces of the chimney prostheses 90, an outer surface of the main graft portion 16, endoluminal prosthesis 12 and an inner surface of the patient's vessel 9 being treated. Such enhanced sealing may reduce or prevent leaks caused by gutter type channels being formed between these surfaces during deployment of these prostheses 12. For some such chimney graft deployment embodiments, inflatable balloon embodiments 62 made from non-compliant materials may be more useful for eliminating gutter type channels formed between these surfaces during deployment of these endoluminal prostheses 12.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the embodiments discussed. Although embodiments have been described in substantial detail with reference to one or more specific embodiments, those of ordinary skill in the art will recognize that changes may be made to the embodiments specifically disclosed in this application, yet these modifications and improvements are within the scope and spirit of the disclosure.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

Certain embodiments are set forth in the claim(s) that follow(s).

What is claimed is:

1. A delivery system for treatment of a vascular defect, comprising:
   an endoluminal prosthesis for treatment of the vascular defect including:
   a tubular main graft portion including a thin flexible material, a main inner lumen, a proximal end and a distal end, and
   a self-expanding anchor member with a distal end thereof being secured to the proximal end of the tubular main graft portion; and a delivery catheter, comprising:
   an elongate shaft including a distal section and a proximal section, the proximal section being configured to releasably secure the endoluminal prosthesis in a constrained state, and
   an inflatable balloon secured to the elongate shaft and disposed within the main inner lumen of the tubular main graft portion of the endoluminal prosthesis in an axial position wherein a proximal end of an inflatable section of the inflatable balloon is disposed adjacent but distal of the self-expanding anchor member, and wherein the elongate shaft comprises an elongate multi-lumen member extending from a distal section of the elongate shaft to a proximal section of the elongate shaft, the multi-lumen member comprising an inflation lumen for inflation of the inflatable balloon, a guidewire lumen and a release member lumen.

2. The delivery system of claim 1 wherein the endoluminal prosthesis further comprises a plurality of radiopaque markers which are circumferentially disposed adjacent the proximal end of the tubular main graft portion and a proximal end of the inflatable section of the inflatable balloon is disposed adjacent but distal of the radiopaque markers.

3. The delivery system of claim 1 wherein a proximal portion of the main graft portion of the endoluminal prosthesis comprises an inflatable cuff and the inflatable balloon is axially disposed such that a working length of the inflatable balloon is axially coextensive with the inflatable cuff.

4. The delivery system of claim 1 wherein the delivery catheter further comprises an outer sheath disposed over the elongate shaft and configured to removably cover the endoluminal prosthesis in the constrained state.

5. The delivery system of claim 1 wherein the endoluminal prosthesis comprises an inflatable endoluminal prosthesis an inflatable portion and wherein the delivery catheter further comprises a fill tube including a fill tube lumen in fluid communication with the inflatable portion of the inflatable endoluminal prosthesis and extending axially within the elongate shaft.

6. The delivery system of claim 1 wherein the inflation lumen comprises an oval cross section.

7. The delivery system of claim 1 wherein the self-expanding anchor member comprises a superelastic metal.

8. The delivery system of claim 1 wherein the self-expanding anchor member comprises a cylindrical stent including an elongate superelastic element disposed in a zig-zag configuration.

9. The delivery system of claim 1 wherein the self-expanding anchor member comprises a monolithic structure formed from a single piece of continuous material with no joints formed therein.

10. The delivery system of claim 1 wherein the self-expanding anchor member comprises barbs including sharp tissue penetrating tips.

11. The delivery system of claim 1 wherein the inflatable balloon comprises an outer transverse dimension of about 10 mm to about 26 mm.

12. The delivery system of claim 1 wherein the inflatable balloon comprises a working length of about 15 mm to about 40 mm.

13. The delivery system of claim 1 wherein the inflatable balloon comprises a compliant material.

14. The delivery system of claim 1 wherein the inflatable balloon comprises a substantially non-compliant material.

15. The delivery system of claim 1 wherein the inflatable balloon comprises a material selected from the group consisting of polyethylene terephthalate, polyamides, polyether block amides, polyethylene, polyurethane and polyvinylchloride.

16. The delivery system of claim 1 wherein a double wall thickness of the inflatable balloon is about 0.001 inches to about 0.003 inches.

* * * * *